United States Patent
Saito et al.

(10) Patent No.: US 9,616,421 B2
(45) Date of Patent: Apr. 11, 2017

(54) CATALYST FOR OLEFIN MULTIMERIZATION AND METHOD FOR PRODUCING OLEFIN MULTIMER IN PRESENCE OF CATALYST FOR OLEFIN MULTIMERIZATION

(71) Applicant: Mitsui Chemicals, Inc., Minato-ku, Tokyo (JP)

(72) Inventors: Yasunori Saito, Ichihara (JP); Atsushi Shibahara, Chiba (JP); Isao Hara, Kanagawa (JP); Kazumori Kawamura, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/770,700

(22) PCT Filed: Feb. 26, 2014

(86) PCT No.: PCT/JP2014/054690
§ 371 (c)(1),
(2) Date: Aug. 26, 2015

(87) PCT Pub. No.: WO2014/133005
PCT Pub. Date: Sep. 4, 2014

(65) Prior Publication Data
US 2016/0001278 A1    Jan. 7, 2016

(30) Foreign Application Priority Data
Feb. 27, 2013  (JP) ................................ 2013-037253

(51) Int. Cl.
*C08F 4/76* (2006.01)
*C08F 4/64* (2006.01)
(Continued)

(52) U.S. Cl.
CPC ......... *B01J 31/1805* (2013.01); *B01J 31/143* (2013.01); *B01J 31/189* (2013.01);
(Continued)

(58) Field of Classification Search
CPC .. C08F 4/02; C08F 4/52; C08F 4/6011; C08F 4/6012; C08F 4/60124; C08F 4/6028;
(Continued)

(56) References Cited

U.S. PATENT DOCUMENTS 5,155,080 A   10/1992  Elder et al.
5,321,106 A    6/1994  LaPointe
(Continued)

FOREIGN PATENT DOCUMENTS

CN    1613881 A    5/2005
CN  101709097 A    5/2010
(Continued)

OTHER PUBLICATIONS

Andes, et al., "New Tantalum-Based Catalyst System for the Selective Trimerization of Ethene to 1-Hexene," J. Am. Chem. Soc. vol. 123, No. 30, Aug. 1, 2001, pp. 7423-7424.
(Continued)

*Primary Examiner* — Rip A Lee
(74) *Attorney, Agent, or Firm* — Foley & Lardner LLP

(57) ABSTRACT

The objectives of the present invention are to provide an olefin oligomerization catalyst that allows properties of particles of a polymer component by-produced in an α-olefin production process to be obtained in such a shape that does not negatively affect a separation process for the particles and to provide a method for producing an olefin oligomer performed in the presence of the olefin oligomerization catalyst. The objectives can be achieved by the olefin oligomerization catalyst obtained by contacting (D) a transition metal compound with a preliminary contact solid
(Continued)

catalyst component (II) obtained by contacting a solid catalyst component (I) formed by supporting (B) an organoaluminum oxy-compound (b-2) on (A) a solid carrier with (C) at least one compound selected from the group consisting of an organometallic compound (c-1), an organoaluminum oxy-compound (c-2), and a compound (c-3) that reacts with the transition metal compound (D) to form a pair of ion.

6 Claims, 2 Drawing Sheets

(51) Int. Cl.
    *B01J 31/18*     (2006.01)
    *C07C 2/32*     (2006.01)
    *C07F 7/28*     (2006.01)
    *B01J 31/14*     (2006.01)
    *B01J 31/22*     (2006.01)
    *C08F 4/60*     (2006.01)

(52) U.S. Cl.
    CPC ............ *B01J 31/2243* (2013.01); *C07C 2/32* (2013.01); *C07F 7/28* (2013.01); *B01J 2231/20* (2013.01); *B01J 2531/46* (2013.01); *B01J 2531/62* (2013.01); *C07C 2531/14* (2013.01); *C07C 2531/22* (2013.01); *C08F 4/60158* (2013.01)

(58) Field of Classification Search
CPC .. C08F 4/6411; C08F 4/6428; C08F 4/60158; B01J 21/08; B01J 31/38; B01J 37/024; B01J 2231/20
See application file for complete search history.

(56) References Cited

U.S. PATENT DOCUMENTS

| | | |
|---|---|---|
| 5,387,568 A | 2/1995 | Ewen et al. |
| 5,519,100 A | 5/1996 | Ewen et al. |
| 5,614,457 A | 3/1997 | Ewen et al. |
| 5,663,249 A | 9/1997 | Ewen et al. |
| 5,840,645 A * | 11/1998 | Ohno ..................... C08F 10/00 502/103 |
| 5,856,257 A | 1/1999 | Freeman et al. |
| 5,883,202 A | 3/1999 | Ewen et al. |
| 6,031,145 A | 2/2000 | Commereuc et al. |
| 6,455,648 B1 | 9/2002 | Freeman et al. |
| 6,459,007 B1 | 10/2002 | Santi et al. |
| 2002/0107345 A1 | 8/2002 | Ittel et al. |
| 2003/0100441 A1 | 5/2003 | Ittel et al. |
| 2003/0114623 A1 | 6/2003 | Mitani et al. |
| 2003/0166456 A1 | 9/2003 | Wass |
| 2004/0097772 A1 | 5/2004 | Deckers et al. |
| 2005/0020788 A1 | 1/2005 | Wass |
| 2005/0065302 A1 | 3/2005 | Mitani et al. |
| 2006/0128910 A1 | 6/2006 | Blann et al. |
| 2006/0173226 A1 | 8/2006 | Blann et al. |
| 2006/0211903 A1 | 9/2006 | Blann et al. |
| 2006/0229480 A1 | 10/2006 | Blann et al. |
| 2007/0093622 A1 | 4/2007 | Yanagawa et al. |
| 2009/0118426 A1 | 5/2009 | Mitani et al. |
| 2011/0082325 A1* | 4/2011 | Suzuki ............... B01J 31/143 585/511 |
| 2013/0059990 A1 | 3/2013 | Kaji et al. |
| 2013/0345376 A1* | 12/2013 | Luo ..................... C08F 10/00 526/130 |

FOREIGN PATENT DOCUMENTS

| | | |
|---|---|---|
| EP | 0 427 696 A2 | 5/1991 |
| EP | 0 427 697 A2 | 5/1991 |
| JP | H01-501950 A | 7/1989 |
| JP | H01-502036 A | 7/1989 |
| JP | H03-179005 A | 8/1991 |
| JP | H03-179006 A | 8/1991 |
| JP | H03-207703 A | 9/1991 |
| JP | H03-207704 A | 9/1991 |
| JP | H06-032745 A | 2/1994 |
| JP | H06-239920 A | 8/1994 |
| JP | H11-019518 A | 1/1999 |
| JP | 2004-502527 A | 1/2004 |
| JP | T-2004-524959 | 8/2004 |
| JP | 2005-152889 A | 6/2005 |
| JP | 2006-117642 A | 5/2006 |
| JP | 2006-516265 A | 6/2006 |
| JP | 2006-517528 A | 7/2006 |
| JP | 2011-178682 A | 9/2011 |
| JP | 2012-072412 A | 4/2012 |
| WO | WO-88/05792 A1 | 8/1988 |
| WO | WO-88/05793 A1 | 8/1988 |
| WO | WO-01/44324 A2 | 6/2001 |
| WO | WO-01/68572 A1 | 9/2001 |
| WO | WO-2009/005003 A1 | 1/2009 |
| WO | WO-2011/142400 A1 | 11/2011 |
| WO | WO-2013/022108 A1 | 2/2013 |

OTHER PUBLICATIONS

Dixon, et al., "Advances in selective ethylene trimerisation—a critical overview," Journal of Organometallic Chemistry, vol. 689, Issue 23, Nov. 2004, pp. 3641-3668.
Hu, et al., "Synthesis and Characterization of Novel Tridentate [NOP] Titanium Complexes and Their Application to Copolymerization and Polymerization of Ethylene," Organometallics, vol. 23, No. 8, Apr. 12, 2004, pp. 1684-1688.
International Search Report dated May 20, 2014 issued in Application No. PCT/JP2014/054690.
McGuinnes, David S., "Olefin Oligomerization via Metallacycles: Dimerization, Trimerization, Tetramerization, and Beyond," Chemical Reviews, vol. 111, 2011, pp. 2321-2341.
Pennington, et al., "The synthesis, structure and ethene polymerization catalysis of mono(salicylaldiminato) titanium and zirconium complexes," Dalton Transactions, No. 3, Feb. 7, 2005, pp. 561-571.
Wang, et al., "Synthesis and Characterization of Titanium(IV) Complexes Bearing Monoanionic [O-NX] (X=O, S, Se) Tridentate Ligands and Their Behaviors in Ethylene Homo- and Copolymerization with 1-Hexene," Organometallics, vol. 25, Jun. 19, 2006, pp. 3259-3266.
Office Action issued in Chinese Patent Application No. 201480008491.2 dated Jun. 20, 2016.

* cited by examiner

CATALYST FOR OLEFIN MULTIMERIZATION AND METHOD FOR PRODUCING OLEFIN MULTIMER IN PRESENCE OF CATALYST FOR OLEFIN MULTIMERIZATION

CROSS REFERENCE TO RELATED APPLICATIONS

This application is the National Phase of PCT/JP2014/054690, filed Feb. 26, 2014, which claims priority to Japanese Application No. 2013-037253, filed Feb. 27, 2013, the contents of which are hereby incorporated by reference in their entirety.

TECHNICAL FIELD

The present invention relates to an olefin oligomerization catalyst and a method for producing an olefin oligomer performed in the presence of the catalyst.

BACKGROUND ART

α-olefins, which serve, for example, as raw material for polyolefin, are important compounds widely used in industrial fields. Among them, 1-hexene is highly demanded, particularly as raw material for polyolefin, and a method for producing 1-hexene with high industrial efficiency in production cost, productivity, and the like has been desired. However, most of methods for producing an industrial polyolefin exhibit insufficient catalytic reactivity (for example, see Patent Literature 1 to 3 and Non-Patent Literature 1 and 2).

Under such circumstances, the present applicant has already reported a novel catalyst that shows high efficiency in α-polyolefin production (see Patent Literature 4).

In addition, in order to simplify a reaction process in production of α-olefin, there have been used catalysts prepared by supporting a transition metal compound on a solid carrier (for example, see Patent Literature 5 to 7).

CITATION LIST

Patent Literature

[Patent Literature 1] U.S. Pat. No. 5,856,257
[Patent Literature 2] JP-T-2004-524959
[Patent Literature 3] WO 01/68572
[Patent Literature 4] WO 2009/5003
[Patent Literature 5] JP-A-2006-117642
[Patent Literature 6] JP-T-2004-502527
[Patent Literature 7] JP-T-2006-517528

Non-Patent Literature

[Non-Patent Literature 1] Journal of American Chemical Society, 2001, vol. 123, pp. 7423-7424.
[Non-Patent Literature 2] Journal of Organometallic Chemistry, 2004, vol. 689, pp. 3641-3668.

SUMMARY OF INVENTION

Technical Problem

The present inventors produced a catalyst formed by supporting a transition metal compound on a solid carrier, as disclosed in Patent Literature 5 to 7 mentioned above, in order to simplify a reaction process in production of α-olefin regarding an olefin oligomerization catalyst disclosed in Patent Literature 4 developed by the inventors themselves, and performed ethylene trimerization reaction as an example.

However, it has been found that production of 1-hexene by the ethylene trimerization reaction using such a catalyst causes by-production of hollow polyethylene particles. In the production process of α-olefin, it is difficult to separate and dry the polyethylene particles using any existing device. Thus, there has been a problem in that the production process is complicated.

Objectives to be achieved by the present invention in view of the problem described above is to provide an olefin oligomerization catalyst that allows properties of particles of a polymer component by-produced in a production process for α-olefin to be obtained in such a shape that does not negatively affect separation and drying processes for the particles, and to provide a method for producing an olefin oligomer performed in the presence of the olefin oligomerization catalyst.

Solution to Problem

The present inventors conducted intensive and extensive studies to solve the above problem, and as a result of which, found that an olefin oligomerization catalyst obtained by contacting a transition metal compound with a preliminary contact solid catalyst component prepared by a specific preparation process allows particle properties of a polymer component by-produced in an α-olefin production process to be obtained in such a shape that does not negatively affect separation and drying processes for the particles, and thereby completed the present invention.

Specifically, the present invention relates to the following [1] to [7]:

[1] An olefin oligomerization catalyst (III) obtained by contacting (D) a transition metal compound having a transition metal atom selected from Group III to Group X of the periodic table with a preliminary contact solid catalyst component (II) obtained by contacting a solid catalyst component (I) formed by supporting (B) an organoaluminum oxy-compound (b-2) on (A) a solid carrier with (C) at least one compound selected from the group consisting of an organometallic compound (c-1), an organoaluminum oxy-compound (c-2), and a compound (c-3) that reacts with the transition metal compound (D) to form a pair of ions.

[2] The olefin oligomerization catalyst (III) according to [1], in which as the component (B), an organoaluminum compound (b-1) is further used.

[3] The olefin oligomerization catalyst (III) according to [1] or [2], in which the component (C) is the organoaluminum oxy-compound (c-2).

[4] The olefin oligomerization catalyst (III) according to any one of [1] to [3], in which the transition metal compound (D) is a transition metal compound having a transition metal atom selected from Group III to Group VI of the periodic table.

[5] The olefin oligomerization catalyst (III) according to any one of [1] to [3], in which the transition metal compound (D) is represented by general formula (1) below:

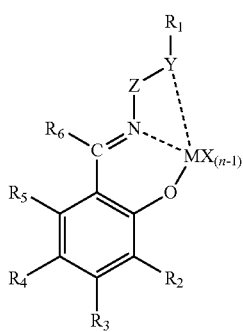

(1)

(in the general formula (1), $R^1$ to $R^6$ may be the same as or different from each other and each represent a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group, or a tin-containing group, in which two or more thereof may be linked to each other, and $R^1$ may be linked to Z;

M represents a transition metal atom selected from Group III to Group X of the periodic table;

n represents a valence of M;

X represents a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group, or a tin-containing group, in which atoms or groups represented by X may be the same as or different from each other, and the groups represented by X may be liked to each other to form a ring;

Y represents an oxygen atom, a nitrogen atom, a phosphorus atom, or a sulfur atom;

Z represents a hydrocarbon group or a heterocyclic compound residue that may have a substituent, and the minimum number of bonds linking Y and N is 4 to 6;

In the formula, a bond linking Y and Z may be a double bond or a triple bond, and a bond linking Y and $R^1$ may be a double bond or a triple bond; and additionally, in the formula, each dotted line represents a coordination bond).

[6] A method for producing an olefin oligomer, in which an oligomerization reaction of an olefin is performed in the presence of the olefin oligomerization catalyst (III) according to any one of [1] to [5].

[7] The method for producing an olefin oligomer according to [6], in which the olefin is ethylene, and the olefin oligomer is 1-hexene.

Advantageous Effects of Invention

Use of the olefin oligomerization catalyst according to the present invention allows particles of a polymer compound by-produced in an olefin oligomerization reaction not to be hollow, thus allowing the simplification of the production process.

DESCRIPTION OF EMBODIMENTS

Figure 1:
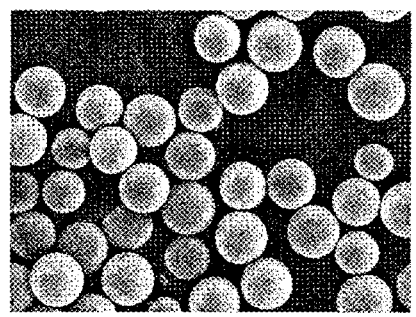
FIG. 1 is an electromicroscopic photograph (200 times) of a solid catalyst component (I-1) prepared in Example 1.

An olefin oligomerization catalyst used in the present invention can be produced in a method as described below.

In the present invention, oligomerization of olefin means dimerization to decamerization of olefin, preferably dimerization to hexamerization of olefin, and more preferably dimerization to tetramerization of olefin.

An olefin oligomerization catalyst (III) according to the present invention is obtained by contacting (D) a transition metal compound with a preliminary contact solid catalyst component (II) obtained by contacting a solid catalyst component (I) described later formed by supporting (B) an organoaluminum oxy-compound (b-2) on (A) a solid carrier with (C) at least one compound selected from the group consisting of an organometallic compound (c-1), an organoaluminum oxy-compound (c-2), and a compound (c-3) that reacts with the transition metal compound (D) to form a pair of ions.

Hereinafter, each constituent component will be described.

[Solid Catalyst Component (I)]

In the present invention, the solid catalyst component (I) is obtained by supporting the organoaluminum oxy-compound (b-2) as the component (B) on the solid carrier (A). More preferably, the solid catalyst component (I) is obtained by further supporting an organoaluminum compound (b-1) in addition to the organoaluminum oxy-compound (b-2) as the component (B) on the solid carrier (A).

Hereinafter, a detailed description will be given of the solid carrier (A), and (B) the organoaluminum oxy-compound (b-2) and the organoaluminum compound (b-1).

<(A) Solid Carrier>

The solid carrier (A) used in the present invention is a granular or fine particle solid formed from an inorganic compound or an organic compound.

Examples of the inorganic compound include inorganic oxides, inorganic halides, clays, a clay minerals, and ion-exchangeable layered compounds.

Examples of the inorganic oxides (excluding alkali metal oxides) include $SiO_2$, $Al_2O_3$, MgO, ZrO, $TiO_2$, $B_2O_3$, CaO, ZnO, BaO, and $ThO_2$. In addition, there are also mentioned, as the inorganic oxides, for example, composite oxides including the aforementioned inorganic oxides, such as natural zeolite, synthetic zeolite, $SiO_2$—MgO, $SiO_2$—$Al_2O_3$, $SiO_2$—$TiO_2$, $SiO_2$—$V_2O_5$, $SiO_2$—$Cr_2O_3$, and $SiO_2$—$TiO_2$—MgO. Additionally, the aforementioned inorganic oxides may be mixtures of these inorganic oxides.

Among them, preferred are inorganic oxides containing, as a main ingredient, at least one selected from $SiO_2$ and $Al_2O_3$, and more preferably $SiO_2$. The main ingredient means an ingredient having a highest weight ratio in cases where a plurality of inorganic oxides are contained.

The inorganic oxides may contain a small amount of a secondary ingredient, for example, a carbonate such as $Na_2CO_3$, $K_2CO_3$, $CaCO_3$, or $MgCO_3$; a sulphate such as $Na_2SO_4$, $Al_2(SO_4)_3$, or $BaSO_4$; a nitrate such as $KNO_3$, $Mg(NO_3)_2$, or $Al(NO_3)_3$; or an alkali metal oxide such as $Na_2O$, $K_2O$, or $Li_2O$.

Properties of the solid carrier formed from any of the inorganic oxides vary depending on the kind of the inorganic oxide, the production method therefor, and the like. The solid carrier has a particle size ranging usually from 0.5 to 300 μm, and a specific surface area ranging usually from 50 to 1000 m$^2$/g. In addition, the carrier formed from any of the inorganic oxides is typically porous, and has a pore volume ranging preferably from 0.3 to 3.0 cm$^3$/g. The carrier having such properties is optionally fired at 100 to 1000° C. and used.

Examples of the inorganic halides include $MgCl_2$, $MgBr_2$, $MnCl_2$, and $MnBr_2$. Any of the inorganic halides that has a granular or fine particle shape can be directly used as the solid carrier, but may be optionally pulverized by a ball mill, a vibration mill, or the like before being used as the solid carrier. Alternatively, there may be used fine particles obtained by dissolving any of the inorganic halides in a solvent such as alcohol and precipitating with a precipitation agent.

The clays are those usually made of a clay mineral as a main ingredient. In addition, the ion-exchangeable layered compounds are those having a crystal structure in which planes formed by an ionic bonding or the like are laminated in parallel to each other with a weak bonding force, and in which the contained ions are exchangeable. Most clay minerals are ion-exchangeable layered compounds. Additionally, the clays, the clay minerals, and the ion-exchangeable layer compounds that can be used are not limited to natural ones but can also be synthetic ones.

Examples of the crystal structure of the ion-exchangeable layered compounds include layered crystal structures such as a hexagonal close-packed structure, an antimony structure, a $CdCl_2$ structure, and a $CdI_2$ structure.

Examples of the clays and the clay minerals include kaolin, bentonite, kibushi clay, gairome clay, allophane, hisingerite, pyrophyllite, mica, montmorillonite, vermiculite, chlorite, palygorskite, kaolinite, nacrite, dickite, and halloysite.

Examples of the ion-exchangeable layered compounds include crystalline acid salts of multivalent metals, such as α-Zr(HAsO$_4$)$_2$·H$_2$O, α-Zr(KPO$_4$)$_2$·3H$_2$O, α-Ti(HPO$_4$)$_2$, α-Ti(HAsO$_4$)$_2$·H$_2$O, α-Sn(HPO$_4$)$_2$·H$_2$O, γ-Zr(HPO$_4$)$_2$, γ-Ti(HPO$_4$)$_2$, and γ-Ti(NH$_4$PO$_4$)$_2$·H$_2$O.

Such clays, clay minerals, and ion-exchangeable layered compounds have a pore volume of preferably not less than 0.1 cc/g, and particularly preferably 0.3 to 5 cc/g as measured by mercury intrusion porosimetry in pores with a pore radius of not less than 20 angstroms. Herein, the pore volume is measured in a pore radius range of 20 to 3×10$^4$ angstroms by the mercury intrusion porosimetry that uses a mercury porosimeter. When a material whose volume of pores with a radius of not less than 20 angstroms is less than 0.1 cc/g is used as the carrier, it tends to be difficult to obtain high oligomerization activity.

It is also preferable to perform a chemical treatment on the clays and the clay minerals. The chemical treatment is not particularly limited, and examples thereof include a surface treatment for removing impurities attached to a surface of a clay or clay mineral that is to be used and a treatment for giving an influence on the crystal structure of the clay or the clay mineral. Examples of the chemical treatment include acid treatment, alkaline treatment, salt treatment, and organic substance treatment. Performing acid treatment, for example, removes impurities on the surface of the clay or the clay mineral, as well as allows elution of cations such as Al, Fe, and Mg in the crystal structure included in the clay or the clay mineral, thereby increasing a surface area of the clay or the clay mineral. Performing alkaline treatment, for example, breaks the crystal structure included in the clay or the clay mineral, changing the crystal structure. Alternatively, performing salt treatment or organic substance treatment, for example, forms an ion complex, a molecular complex, an organic derivative, or the like, allowing a change of the surface area of the clay or the clay mineral. In addition, when an ion-exchangeable layered compound is included in the clay or the clay mineral, an interlayer distance therebetween can be changed.

The ion-exchangeable layered compound used in the present invention may be a layered compound whose interlayer distance has been enlarged by exchanging an interlayer exchangeable ion with another bulky (large) ion through the use of ion exchangeable properties thereof. Such a bulky ion plays a supportive role in supporting the layered structure, and is usually called as pillar. In addition, the introduction of another substance (for example, a guest compound or a guest ion) between the layers of a layered compound as mentioned above is referred to as intercalation. Examples of a guest compound and a guest ion to be intercalated include cationic inorganic compounds such as $TiCl_4$ and $ZrCl_4$; metal alkoxides such as $Ti(OR)_4$, $Zr(OR)_4$, $PO(OR)_3$, and $B(OR)_3$ (R represents a hydrocarbon group or the like); and metal hydroxide ions such as $[Al_{13}O_4(OH)_{24}]^{7+}$, $[Zr_4(OH)_{14}]^{2+}$, and $[Fe_3O(OCOCH_3)_6]^+$. These guest compounds and guest ions are used alone or in a combination of two or more thereof.

In addition, in the intercalation of these guest compounds and guest ions, a dimer obtained by hydrolyzing a metal alkoxide such as $Si(OR)_4$, $Al(OR)_3$, or $Ge(OR)_4$ (R represents a hydrocarbon group or the like) or the like, a colloidal inorganic compound such as $SiO_2$, or like may be allowed to coexist. Additionally, examples of the pillar include oxides generated by intercalating the aforementioned metal hydroxide ions between the layers and then thermally dehydrating.

The clay, the clay mineral, and the ion-exchangeable layered compound used in the present invention can be directly used as the solid carrier as long as they have a granular or fine particle shape. Alternatively, before using as the solid carrier, the clay, the clay mineral, and the ion-exchangeable layered compound may be optionally additionally pulverized using a ball mill or the like, sifting, or the like. Additionally, alternatively, the clay, the clay mineral, and the ion-exchangeable layered compound may be used by newly adding water to allow them to adsorb the water or thermally dehydrating. These operations may be performed alone or in a combination of two or more thereof.

Among the clays, clay minerals, and ion-exchangeable layered compounds, preferred are clays and clay minerals, and particularly preferred are montmorillonite, vermiculite, hectorite, taeniolite, and synthetic mica.

Solid carriers formed from the inorganic compounds described above are used alone or in a combination of two or more thereof.

Examples of the organic compounds include (co)polymers generated by containing, as a main ingredient, α-olefin having 2 to 14 carbon atoms, such as ethylene, propylene, 1-butene, or 4-methyl-1-pentene, (co) polymers generated by containing, as a main ingredient, vinylcyclohexane or styrene, and modified products thereof. Examples of the solid carrier formed from an organic compound include granular or fine particle solids formed from the above compounds. These granular or fine particle solids have a particle size ranging from 10 to 300 µm.

<(b-2) Organoaluminum Oxy-Compound>

In the present invention, the organoaluminum oxy-compound (b-2) included in the component (B) supported on the solid carrier (A) may be a conventionally known organoaluminum oxy-compound (aluminoxane), and for example, may be a benzene-insoluble organoaluminum oxy-compound as exemplified in JP-A-H2-78687.

The above organoaluminum oxy-compound can be produced, for example, by methods as below, and is usually obtained as a solution included in a hydrocarbon solvent.

(1) A method in which an organoaluminum compound such as trialkylaluminum is added to a hydrocarbon medium suspension of a compound containing adsorbed water or a salt containing water of crystallization, such as magnesium chloride hydrate, copper sulfate hydrate, aluminum sulfate hydrate, nickel sulfate hydrate, or cerous chloride hydrate to react the organoaluminum compound with the adsorbed water or the water of crystallization.

(2) A method in which water, ice, or water vapor is allowed to directly act on an organoaluminum compound such as trialkylaluminum in a medium such as benzene, toluene, ethyl ether or tetrahydrofuran.

(3) A method in which an organoaluminum compound such as trialkylaluminum is allowed to react with an organotin oxide such as dimethyltin oxide or dibutyltin oxide in a medium such as decane, benzene, or toluene.

The organoaluminum oxy-compound may contain a small amount of another organic metal component. In addition, a solvent or unreacted organoaluminum compound may be distilled away from the above organoaluminum oxy-compound solution produced, and then the organoaluminum oxy-compound may be redissolved in a solvent or suspended in a poor solvent for the organoaluminum oxy-compound.

Examples of the organoaluminum compound used to prepare the organoaluminum oxy-compound include the same organoaluminum compounds as those exemplified as organoaluminum compounds belonging to the compound (b-1) that will be described later.

Among them, preferred are trialkylaluminum and tricycloalkylaluminum, and particularly preferred is trimethylaluminum.

The above organoaluminum compounds are used alone or in a combination of two or more thereof.

Examples of the solvent used to prepare the organoaluminum oxy-compound include aromatic hydrocarbons such as benzene, toluene, xylene, cumene, and cymene; aliphatic hydrocarbons such as pentane, hexane, heptane, octane, decane, dodecane, hexadecane, and octadecane; alicyclic hydrocarbons such as cyclopentane, cyclohexane, cyclooctane, and methylcyclopentane; petroleum fractions such as gasoline, kerosene, and gas oil; and halides of hydrocarbons such as the aromatic hydrocarbons, the aliphatic hydrocarbons, or the alicyclic hydrocarbons mentioned above, particularly hydrocarbons such as chlorides and bromides and halogenated hydrocarbons. In addition, examples of the solvent also include ethers such as ethyl ether and tetrahydrofuran. Among these solvents, particularly preferred are the aromatic hydrocarbons and the aliphatic hydrocarbons.

The aforementioned benzene-insoluble organoaluminum oxy-compound is a compound that is insoluble or slightly soluble in benzene and in which an Al component that dissolves in benzene at 60° C. is contained in an amount of usually 10% or less, preferably 5% or less, and particularly preferably 2% or less in terms of Al atom.

In addition, examples of the organoaluminum oxy-compounds include boron-containing organoaluminum oxy-compounds represented by general formula (ii) below:

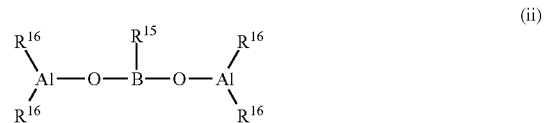

(in the formula (ii), $R^{15}$ represents a hydrocarbon group having 1 to 10 carbon atoms; $R^{16}$, which may be the same as or different from each other, each represent a hydrogen atom, a halogen atom, or a hydrocarbon group having 1 to 10 carbon atoms).

The boron-containing organoaluminum oxy-compounds represented by the general formula (ii) can be produced by reacting an alkylboronic acid represented by general formula (iii) below with an organoaluminum oxy-compound in an inert solvent under an inert gas atmosphere at a temperature of −80° C. to room temperature for 1 minute to 24 hours.

$$R^{15}\text{—B(OH)}_2 \quad \text{(iii)}$$

(in the formula (iii), $R^{15}$ represents the same group as that in the above formula (ii)).

Examples of the alkylboronic acids represented by the general formula (iii) include methylboronic acid, ethylboronic acid, isopropylboronic acid, n-propylboronic acid, n-butylboronic acid, isobutylboronic acid, n-hexylboronic acid, cyclohexylboronic acid, phenylboronic acid, 3,5-difluorophenylboronic acid, pentafluorophenylboronic acid, and 3,5-bis(trifluoromethyl)phenylboronic acid. Among them, preferred are methylboronic acid, n-butylboronic acid, isobutylboronic acid, 3,5-difluorophenylboronic acid, and pentafluorophenylboronic acid. These compounds are used alone or in a combination of two or more thereof.

Examples of the organoaluminum compounds to be reacted with the alkylboronic acids include the same organoaluminum compounds as those exemplified as organoaluminum compounds belonging to the compound (b-1) that will be described later. Among them, preferred are trialkylaluminum and tricycloalkylaluminum, and more preferably, trimethylaluminum, triethylaluminum, and triisobutylaluminum. These compounds are used alone or in a combination of two or more thereof.

These organoaluminum oxy-compounds (b-2) are used alone or in a combination of two or more thereof.

<(b-1) Organoaluminum Compound>

Examples of the organoaluminum compound (b-1) that is optionally used as the compound (B) in the present invention include compounds represented by general formula (i) below:

$$R^{a}_{m}Al(OR^{b})_{n}H_{p}X_{q} \quad \text{(i)}$$

(in the formula (i), $R^a$ and $R^b$, which may be the same as or different from each other, each represent a hydrocarbon group having 1 to 15, and preferably 1 to 4 carbon atoms; X represents a halogen atom; $0<m\leq3$, $0\leq n<3$, $0\leq p<3$, $0\leq q<3$, and $m+n+p+q=3$).

Examples of the above organoaluminum compounds (b-1) include compounds as below:

Organoaluminum compounds represented by general formula:

$$R^{a}_{m}Al(OR^{b})_{3-m} \quad \text{(i-1)}$$

(in the formula (i-1), $R^a$ and $R^b$, which may be the same as or different from each other, each represent a hydrocarbon group having 1 to 15, and preferably 1 to 4 carbon atoms; 0<m≤3, and preferably 1.5≤m≤3);

organoaluminum compounds represented by general formula:

$$R^a_m AlX_{3-m} \quad (i-2)$$

(in the formula (i-2), $R^a$ represents a hydrocarbon group having 1 to 15, and preferably 1 to 4 carbon atoms; X represents a halogen atom; 0<m≤3, and preferably 0<m<3);

organoaluminum compounds represented by general formula:

$$R^a_m AlH_{3-m} \quad (i-3)$$

(in the formula (i-3), $R^a$ represents a hydrocarbon group having 1 to 15, and preferably 1 to 4 carbon atoms; 0<m≤3, and preferably 2≤m<3); and organoaluminum compounds represented by general formula:

$$R^a_m Al(OR^b)_n X_q \quad (i-4)$$

(in the formula (i-4), $R^a$ and $R^b$, which may be the same as or different from each other, each represent a hydrocarbon group having 1 to 15, and preferably 1 to 4 carbon atoms; X represents a halogen atom; 0<m≤3, 0≤n<3, 0≤q<3, and m+n+q=3).

More specific examples of the organoaluminum compounds (b-1) include tri(n-alkyl)aluminums such as trimethylaluminum, triethylaluminum, tri(n-butyl)aluminum, tripropylaluminum, tripentylaluminum, trihexylaluminum, trioctylaluminum, and tridecylaluminum; tri-(branched-chain alkyl)aluminums such as triisopropylaluminum, triisobutylaluminum, tri(sec-butyl)aluminum, tri(tert-butyl) aluminum, tri(2-methylbutyl)aluminum, tri(3-methylbutyl) aluminum, tri(2-methylpentyl)aluminum, tri(3-methylpentyl)aluminum, tri(4-methylpentyl)aluminum, tri (2-methylhexyl)aluminum, tri(3-methylhexyl)aluminum, and tri(2-ethylhexyl)aluminum; tricycloalkylaluminums such as tricyclohexylaluminum and tricyclooctylaluminum; triarylaluminums such as triphenylaluminum and tritolylaluminum; dialkylaluminum hydrides such as diethylaluminum hydride and diisobutylaluminum hydride; alkenylaluminums such as isoprenylaluminums represented by a formula such as $(iC_4H_9)_x Al_y (C_5H_{10})_z$ (in the formula, x, y, and z each represent a positive value; z≤2x; and $iC_4H_9$ represents an isobutyl group); alkylaluminum alkoxides such as isobutylaluminum methoxide, isobutylaluminum ethoxide, and isobutylaluminum isopropoxide; dialkylaluminum alkoxides such as dimethylaluminum methoxide, diethylaluminum ethoxide, and dibutylaluminum butoxide; alkylaluminum sesquialkoxides such as ethylaluminum sesquiethoxide and butylaluminum sesquibutoxide; partially alkoxylated alkylaluminums having an average composition represented by a formula such as $R^a_{2.5}Al(OR^b)_{0.5}$ (in the formula, $R^a$ and $R^b$, which may be the same as or different from each other, each represent a hydrocarbon group having 1 to 15, and preferably 1 to 4 carbon atoms); dialkylaluminum aryloxides such as diethylaluminum phenoxide, diethylaluminum (2,6-di-tert-butyl-4-methylphenoxide), ethylaluminum bis(2,6-di-tert-butyl-4-methylphenoxide), diisobutylaluminum(2,6-di-tert-butyl-4-methylphenoxide), and isobutylaluminum bis(2,6-di-tert-butyl-4-methylphenoxide); dialkylaluminum halides such as dimethylaluminum chloride, diethylaluminum chloride, dibutylaluminum chloride, diethylaluminum bromide, and diisobutylaluminum chloride; alkylaluminum sesquihalides such as ethylaluminum sesquichloride, butylaluminum sesquichloride, and ethylaluminum sesquibromide; partially halogenated alkylaluminums such as alkylaluminum dihalides including ethylaluminum dichloride, propylaluminum dichloride, and butylaluminum dibromide; dialkylaluminum hydrides such as diethylaluminum hydride and dibutylaluminum hydride; partially hydrogenated alkylaluminums such as alkylaluminum dihydrides including ethylaluminum dihydride and propylaluminum dihydride; and partially alkoxylated and halogenated alkylaluminums such as ethylaluminum ethoxychloride, butylaluminum butoxychloride, and ethylaluminum ethoxybromide.

Among them, from the viewpoint of activity, selectivity, and availability of the catalyst, preferred are trialkylaluminums and tricycloalkylaluminums, and particularly preferred are trimethylaluminum, triethylaluminum, and triisobutylaluminum.

These organoaluminum compounds (b-1) are used alone or in a combination of two or more thereof.

<Method for Preparing Solid Catalyst Component (I)>

The solid catalyst component (I) according to the present invention can be prepared by contacting the solid carrier (A) with the organoaluminum oxy-compound (b-2) as the component (B). The component (B) is preferably a combination of the organoaluminum oxy-compound (b-2) and the organoaluminum compound (b-1).

The preparation method allows the organoaluminum oxy-compound (b-2) to be supported on a surface of the solid carrier (A). In this case, when the organoaluminum compound (b-1) is used in combination as the component (B), a group (for example, an SiOH group in a case in which the solid carrier (A) is $SiO_2$) that exists on the surface of the solid carrier (A) and is highly reactive with the organoaluminum oxy-compound (b-2) is processed by the organoaluminum compound (b-1), so that uneven distribution of the organoaluminum oxy-compound (b-2) can be suppressed to allow the compound to be more evenly supported.

The preparation of the solid catalyst component (I) may use a solvent. The solvent to be used is preferably an organic compound inactive to the solid carrier (A) and the component (B). Examples of such an organic compound include aliphatic hydrocarbons such as propane, butane, hexane, heptane, octane, decane, dodecane, and kerosene; alicyclic hydrocarbons such as cyclopentane, cyclohexane, and methylcyclopentane; aromatic hydrocarbons such as benzene, toluene, and xylene; halogenated hydrocarbons such as ethylene chloride, chlorobenzene, and dichloromethane; and mixtures thereof.

In the preparation of the solid catalyst component (I), (B) the organoaluminum oxy-compound (b-2) is used in an amount of usually $10^{-5}$ to $10^{-1}$ mol, and preferably $2 \times 10^{-5}$ to $5 \times 10^{-2}$ mol per gram of the solid carrier (A) in terms of aluminum atom. Additionally, when the organoaluminum compound (b-1) is further used in combination as the component (B), the organoaluminum compound (b-1) is used, as an upper limit, in an amount of usually $5 \times 10^{-1}$ mol, and preferably $2 \times 10^{-2}$ mol per gram of the solid carrier (A) in terms of aluminum atom.

When the amount of the organoaluminum oxy-compound (b-2) used is less than $10^{-5}$ mol per gram of the solid carrier (A), it is not preferable since catalytic activity becomes insufficient, which is economically disadvantageous. In addition, when the amount of the organoaluminum oxy-compound (b-2) used is more than $10^{-1}$ mol per gram of the solid carrier (A), there is generated an excessive amount of the organoaluminum oxy-compound (b-2) that cannot be supported on the component (A), which is not preferable since it is not only economically disadvantageous but also can result in by-production of an amorphous polymer component in an α-olefin production process, whereby continuous operability can be negatively affected.

When the amount of the organoaluminum compound (b-1) used is more than $5\times10^{-2}$ mol per gram of the solid carrier (A), there is generated an excessive amount of the organoaluminum compound (b-1) that cannot be supported on the component (A), which is not preferable since it is not only economically disadvantageous but also can result in by-production of an amorphous polymer component in an α-olefin production process, whereby continuous operability can be negatively affected.

A temperature of contact of the above-described respective components with each other is usually −50 to 150° C., and preferably −20 to 120° C., and a time length of the contact is 1 to 1000 minutes, and preferably 5 to 600 minutes.

In the solid catalyst component (I) thus obtained, preferably, (B) the organoaluminum oxy-compound (b-2) and the optionally used organoaluminum compound (b-1) are supported in an amount of $10^{-5}$ to $10^{-1}$ mol, and preferably $2\times10^{-5}$ to $5\times10^{-2}$ mol per gram of the solid carrier (A) in terms of aluminum atom.

[Preliminary Contact Solid Catalyst Component (II)]

In the present invention, the preliminary contact solid catalyst component (II) is obtained by contacting the solid catalyst component (I) thus obtained with (C) at least one component selected from the group consisting of the organometallic compound (c-1), the organoaluminum oxy-compound (c-2), and a compound (c-3) that reacts with (D) the transition metal compound that will be described later to form a pair of ions.

In each of the olefin oligomerization catalysts as disclosed in Patent Literature 4 to 7 mentioned above, a transition metal compound is supported on a solid carrier corresponding to the solid catalyst component (I) described above. However, in an olefin oligomerization reaction performed using such a catalyst, there has been observed a phenomenon in which a hollow olefin polymer component is by-produced. An analysis of the catalyst was made to find the reason of the phenomenon, and it was found that a transition metal as a reaction center was significantly unevenly distributed on an outermost surface of the solid carrier. This seems to indicate that a factor for which the by-produced olefin polymer component becomes hollow is that the olefin polymer is by-produced due to the transition metal unevenly distributed on the uppermost surface of the solid carrier in the olefin oligomerization reaction. Then, although a detailed reason for by-production of a hollow olefin polymer is unknown, the reason is assumed to be that since the organoaluminum oxy-compound supported on the uppermost surface of the solid carrier has a high degree of association, a layer derived from such an organoaluminum oxy-compound includes a complex entanglement of molecular chains and therefore there is almost no remaining space that allows the transition metal compound to enter an internal surface of the carrier.

On the other hand, in the preliminary contact solid catalyst component (II) according to the present invention, it is assumed that contacting the solid catalyst component (I) with the component (C) causes recombination of an Al—O—Al bond derived from the organoaluminum oxy-compound supported on the surface of the solid catalyst component (I), and the degree of association of the organoaluminum oxy-compound (b-2) is reduced, whereby the entanglement of molecular chains is reduced to form a space. As a result, in preparation of the olefin oligomerization catalyst (III), it seems that the transition metal compound (D) described later is allowed to be relatively evenly distributed onto the internal surface of the preliminary contact solid catalyst component (II) without staying only on the uppermost surface thereof, so that olefin polymer is generated even from the internal surface thereof in an oligomerization reaction of an olefin. This seems to be able to suppress the by-production of a hollow olefin polymer component.

Hereinafter, a detailed description will be given of each of the organometallic compound (c-1), the organoaluminum oxy-compound (c-2), and a compound (c-3) that reacts with the following transition metal compound (D) to form a pair of ions.

<(c-1) Organometallic Compound>

The organometallic compound (c-1) is an organometallic compound other than the organoaluminum oxy-compound (c-2) described later, and typical examples thereof include organometallic compounds containing a metal selected from Group I of the periodic table (Li, Na, K, Rb, Cs, Fr), Group II thereof (Be, Mg, Ca, Sr, Ba, Ra), Group XII thereof (Zn, Cd, Hg), and Group XIII thereof (Al, Ga, In, Tl). Examples of these organometallic compounds (C-1) include organoaluminum compounds (c-1a), (c-1b), and (c-1c) described below.

(c-1a): Organoaluminum compounds represented by general formula (c-1a) below:

$$R^a{}_m Al(OR^b)_n H_p X_q \quad \text{(c-1a)}$$

(in the formula (c-1a), $R^a$ and $R^b$, which may be the same as or different from each other, each represent a hydrocarbon group having 1 to 15, and preferably 1 to 4 carbon atoms; X represents a halogen atom; $0<m\leq3$, $0\leq n<3$, $0\leq p<3$, $0\leq q<3$, and $m+n+p+q=3$).

(c-1b): Complex alkylated products of a metal of Group I of the periodic table and aluminum represented by general formula (c-1b) below:

$$M^2 AlR^a{}_4 \quad \text{(c-1b)}$$

(in the formula (c-1b), $M^2$ represents Li, Na, or K; and $R^a$ represents a hydrocarbon group having 1 to 15, and preferably 1 to 4 carbon atoms).

(c-1c): Dialkyl compounds of a metal of Group II or XII of the periodic table represented by general formula (c-1c) below:

$$R^a R^b M^3 \quad \text{(c-1c)}$$

(in the formula (c-1c), $R^a$ and $R^b$, which may be the same as or different from each other, each represent a hydrocarbon group having 1 to 15, and preferably 1 to 4 carbon atoms; and $M^3$ represents Mg, Zn, or Cd).

Examples of organoaluminum compounds belonging to the compounds (c-1a) can be the same ones as the above organoaluminum compounds (b-1).

Examples of the compounds belonging to the compounds (c-1b) include $LiAl(C_2H_5)_4$ and $(C_7H_{15})$ Examples of the compounds belonging to the (c-1c) include dimethylmagnesium, diethylmagnesium, dibutylmagnesium, butylethylmagnesium, dimethylzinc, and diethylzinc.

Examples of the organometallic compounds (c-1) other than the compounds (c-1a) to (c-1c) include methyllithium, ethyllithium, propyllithium, butyllithium, methylmagnesium bromide, methylmagnesium chloride, ethylmagnesium bromide, ethylmagnesium chloride, propylmagnesium bromide, propylmagnesium chloride, butylmagnesium bromide, and butylmagnesium chloride.

In addition, the organometallic compounds (c-1) may be combinations of such compounds that allow formation of the above organoaluminum compounds in the above oligomerization reaction system, such as a combination of an aluminum halide and alkyllithium and a combination of an aluminum halide and alkylmagnesium.

Among the organometallic compounds (c-1), preferred are the organoaluminum compounds (c1-a).

The organometallic compounds (c-1) are used alone or in a combination of two or more thereof.

<(c-2) Organoaluminum Oxy-Compound>

Examples of organoaluminum oxy-compounds belonging to the compound (c-2) can be the same ones as the above organoaluminum oxy-compounds (b-2).

Among these compounds, from the viewpoint of activity, selectivity, and availability of the catalyst, methylaluminoxane is particularly preferable.

<(c-3) Compound that Reacts with Transition Metal Compound (D) to Form Pair of Ions>

The compound (c-3) that reacts with the transition metal compound (D) to form a pair of ions is a compound that reacts with the transition metal compound (D) described later to form a pair of ions. Accordingly, at least compounds that are contacted with the transition metal compound (D) to form a pair of ions are included in the compound. The compounds (c-3) that reacts with the transition metal compound (D) to form a pair of ions are hereinafter referred to also as "ionized ionic compounds".

Examples of the ionized ionic compounds belonging to the compounds (C-3) include Lewis acids, ionic compounds, borane compounds, and carborane compounds, as described in JP-A-H1-501950, JP-A-H1-502036, JP-A-H3-179005, JP-A-H3-179006, JP-A-H3-207703, JP-A-H3-207704, U.S. Pat. No. 5,321,106, and the like. Furthermore, examples of the ionized ionic compounds belonging to the above compounds (c-3) also include isopoly acid compounds and heteropoly acid compounds.

Examples of the Lewis acids include compounds represented by $BR_3$ (R represents a phenyl group or fluorine that may have a substituent such as fluorine, a methyl group, or a trifluoromethyl group). Examples of the compounds represented by $BR_3$ include trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron, and tris(3,5-dimethylphenyl)boron.

Examples of the ionic compounds include compounds represented by general formula (iv) below:

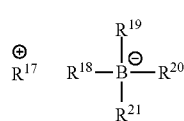

(iv)

In the above formula (iv), $R^{17+}$ represents $H^+$, a carbonium cation, an oxonium cation, an ammonium cation, a phosphonium cation, a cycloheptyltrienyl cation, or a ferrocenium cation containing a transition metal.

Examples of the carbonium cation include tri-substituted carbonium cations such as triphenylcarbonium cation, tri(methylphenyl)carbonium cation, and tri(dimethylphenyl)carbonium cation.

Examples of the ammonium cation include trialkylammonium cations such as trimethylammonium cation, triethylammonium cation, tri(n-propyl)ammonium cation, and tri(n-butyl)ammonium cation; N,N-dialkylanilinium cations such as N,N-dimethylanilinium cation, N,N-diethylanilinium cation, and N,N,2,4,6-pentamethylanilinium cation; and dialkylammonium cations such as di(isopropyl) ammonium cation and dicyclohexylammonium cation.

Specific examples of the phosphonium cation include triarylphosphonium cations such as triphenylphosphonium cation, tri(methylphenyl)phosphonium cation, and tri(dimethylphenyl)phosphonium cation.

$R^{17+}$ preferably represents a carbonium cation, an ammonium cation, or the like, and particularly preferably represents a triphenylcarbonium cation, an N,N-dimethylanilinium cation, or an N,N-diethylanilinium cation.

In the above formula (iv), $R^{18}$ to $R^{21}$ represent organic groups that may be the same as or different from each other, and preferably an aryl group or a substituted aryl group.

Examples of the ionic compounds further include trialkyl-substituted ammonium salts, N,N-dialkylanilinium salts, dialkylammonium salts, and triarylphosphonium salts.

Examples of the trialkyl-substituted ammonium salts include triethylammonium tetraphenylborate, tri(n-propyl) ammonium tetraphenylborate, tri(n-butyl)ammonium tetraphenylborate, trimethylammonium tetra(p-tolyl)borate, trimethylammonium tetra(o-tolyl)borate, tri(n-butyl)ammonium tetra(pentafluorophenyl)borate, tri(n-propyl)ammonium tetra(o,p-dimethylphenyl)borate, tri(n-butyl)ammonium tetra(m,m-dimethylphenyl)borate, tri(n-butyl) ammonium tetra(p-trifluoromethylphenyl)borate, tri(n-butyl)ammonium tetra(3,5-ditrifluoromethylphenyl)borate, and tri(n-butyl)ammonium tetra(o-tolyl)borate.

Examples of the N,N-dialkylanilinium salts include N,N-dimethylanilinium tetraphenylborate, N,N-diethylanilinium tetraphenylborate, and N,N,2,4,6-pentamethylanilinium tetraphenylborate.

Examples of the dialkylammonium salts include di(n-propyl)ammonium tetra(pentafluorophenyl)borate and dicyclohexylammonium tetraphenylborate.

Furthermore, examples of the ionic compounds further include triphenylcarbenium tetrakis(pentafluorophenyl)borate, N,N-dimethylanilinium tetrakis(pentafluorophenyl)borate, ferrocenium tetra(pentafluorophenyl)borate, triphenylcarbenium pentaphenylcyclopentadienyl complex, N,N-diethylanilinium pentaphenylcyclopentadienyl complex, and boron compounds represented by a formula (v) or (vi) below:

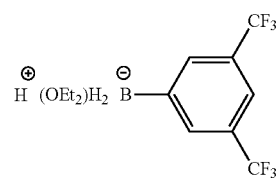

(v)

(in the formula (v), Et represents an ethyl group).

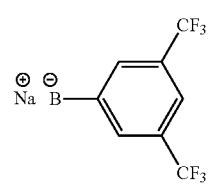

(vi)

Examples of the borane compounds include salts of anions, such as decaborane (14); bis[tri(n-butyl)ammonium] nonaborate, bis[tri(n-butyl)ammonium]decaborate, bis[tri (n-butyl)ammonium]undecaborate, bis[tri(n-butyl)ammonium]dodecaborate, bis[tri(n-butyl)ammonium] decachlorodecaborate, and bis[tri(n-butyl)ammonium] dodecachlorododecaborate; and salts of metal borane anions, such as tri(n-butyl)ammonium bis(dodecahydridododecaborate)cobaltate(III) and bis[tri(n-butyl)ammonium]bis(dodecahydridododecaborate)nickelate(III).

Examples of the carborane compounds include salts of anions, such as 4-carbanonaborane (14) 1,3-dicarbanonaborane (13), 6,9-dicarbadecaborane (14), dodecahydrido-1-phenyl-1,3-dicarbanonaborane, dodecahydrido-1-methyl-1,3-dicarbanonaborane, undecahydrido-1,3-dimethyl-1,3-dicarbanonaborane, 7,8-dicarbaundecaborane (13), 2,7-dicarbaundecaborane (13), undecahydrido-7,8-dimethyl-7,8-dicarbaundecaborane, dodecahydrido-11-methyl-2,7-dicarbaundecaborane, tri(n-butyl)ammonium-1-carbadecaborate, tri(n-butyl)ammonium-1-carbaundecaborate, tri(n-butyl)ammonium-1-carbadodecaborate, tri(n-butyl)ammonium-1-trimethylsilyl-1-carbadecaborate, tri(n-butyl)ammoniumbromo-1-carbadodecaborate, tri(n-butyl)ammonium-6-carbadecaborate (14), tri(n-butyl)ammonium-6-carbadecaborate (12), tri(n-butyl)ammonium-7-carbaundecaborate (13), tri(n-butyl)ammonium-7,8-dicarbaundecaborate (12), tri(n-butyl)ammonium-2,9-dicarbaundecaborate (12), tri(n-butyl)ammonium dodecahydrido-8-methyl-7,9-dicarbaundecaborate, tri(n-butyl)ammonium undecahydrido-8-ethyl-7,9-dicarbaundecaborate, tri(n-butyl)ammonium undecahydrido-8-butyl-7,9-dicarbaundecaborate, tri(n-butyl)ammonium undecahydrido-8-aryl-7,9-dicarbaundecaborate, tri(n-butyl)ammonium undecahydrido-9-trimethylsilyl-7,8-dicarbaundecaborate, and tri(n-butyl)ammonium undecahydrido-4,6-dibromo-7-carbaundecaborate; and metal carborane anions such as tri(n-butyl)ammonium bis(nonahydrido-1,3-dicarbanonaborate)cobaltate(III), tri(n-butyl)ammonium bis(undecahydrido-7,8-dicarbaundecaborate)ferrate(III) tri(n-butyl)ammonium bis(undecahydrido-7,8-dicarbaundecaborate)cobaltate(III), tri(n-butyl)ammonium bis(undecahydrido-7,8-dicarbaundecaborate)nickelate(III), tri(n-butyl)ammonium bis(undecahydrido-7,8-dicarbaundecaborate)cuprate(III), tri(n-butyl)ammonium bis(undecahydrido-7,8-dicarbaundecaborate)aurate(III), tri(n-butyl)ammonium bis(nonahydrido-7,8-dimethyl-7,8-dicarbaundecaborate)ferrate (III), tri(n-butyl)ammonium bis (nonahydrido-7,8-dimethyl-7,8-dicarbaundecaborate) chromate (III), tri(n-butyl)ammonium bis (tribromooctahydrido-7,8-dicarbaundecaborate)cobaltate (III), tris[tri(n-butyl)ammonium]bis(undecahydrido-7-carbaundeca borate)chromate(III), bis[tri(n-butyl)ammonium] bis(undecahydrido-7-carbaundeca borate)manganate(IV), bis[tri(n-butyl)ammonium]bis(undecahydrido-7-carbaundeca borate)cobaltate(III), and bis[tri(n-butyl)ammonium] bis(undecahydrido-7-carbaundeca borate)nickelate(IV).

Isopoly acid compounds are compounds including an isopoly acid skeleton, and are acids produced by condensation of oxoacids of one metal selected from vanadium, niobium, molybdenum, tantalum, tungsten, and the like, or salts thereof. Examples of the isopoly acid compounds include vanadic acid, niobic acid, molybdic acid, tantalic acid, tungstic acid, and salts of these acids. Examples of the salts of the acids include inorganic salts derived from metals, such as metals of Group I of the periodic table (lithium, sodium, potassium, rubidium, cesium, etc.) and metals of Group II of the periodic table (beryllium, magnesium, calcium, strontium, barium, etc.) and the above acids, and organic salts such as salts derived from triphenylethyl groups and the above acids.

The heteropoly acid compounds are compounds including a heteropoly acid skeleton in which any of hetero atoms that are P-block elements (elements belonging to Group XIII to Group XVIII of the periodic table) such as silicon, phosphorus, titanium, germanium, arsenic, and tin has been inserted in the isopoly acid skeleton of at least one metal selected from vanadium, niobium, molybdenum, tantalum, tungsten, and the like. Examples of the heteropoly acid compounds include phosphovanadic acid, germanovanadic acid, arsenovanadic acid, phosphoniobic acid, germanoniobic acid, siliconomolybdic acid, phosphomolybdic acid, titanomolybdic acid, germanomolybdic acid, arsenomolybdic acid, stannomolybdic acid, phosphotungstic acid, germanotungstic acid, stannotungstic acid, phosphomolybdovanadic acid, phosphotungstovanadic acid, germanotungstovanadic acid, phosphomolybdotungstovanadic acid, germanomolybdotungstovanadic acid, phosphomolybdotungstic acid, phosphomolybdoniobic acid; and salts of these acids. Examples of the salts of these acids include inorganic salts derived from metals such as metals of Group I of the periodic table (lithium, sodium, potassium, rubidium, cesium, etc.) and metals of Group II of the periodic table (beryllium, magnesium, calcium, strontium, barium, etc.) and the above acids, and organic salts such as salts derived from triphenylethyl groups and the above acids.

The isopoly acid compounds and the heteropoly acid compounds are used alone or in a combination of two or more thereof.

The ionized ionic compounds belonging to the compounds (c-3) are used alone or in a combination of two or more thereof.

Among the organometallic compound (c-1), the organoaluminum oxy-compound (c-2), and the compound (c-3) that reacts with the below-described transition metal compound (D) to form a pair of ions, the organoaluminum oxy-compound (c-2) is particularly preferably used in the recombination reaction of the Al—O—Al bond derived from the organoaluminum oxy-compound (b-2) supported on the surface of the solid catalyst component (I) described above.

<Method for Preparing Preliminary Contact Solid Catalyst Component (II)>

The preliminary contact solid catalyst component (II) according to the present invention can be prepared by contacting the solid catalyst component (I) with (C) at least one compound selected from the group consisting of the organometallic compound (c-1), the organoaluminum oxy-compound (c-2), and the compound (c-3) that reacts with the below-described transition metal compound (D) to form a pair of ions.

The preparation of the preliminary contact solid catalyst component (II) may use a solvent. The solvent to be used is preferably an organic compound inactive to the solid catalyst component (I) and the component (C), and examples thereof include aliphatic hydrocarbons such as propane, butane, hexane, heptane, octane, decane, dodecane, and kerosene; alicyclic hydrocarbons such as cyclopentane, cyclohexane, and methylcyclopentane; aromatic hydrocarbons such as benzene, toluene, and xylene; halogenated hydrocarbons such as ethylene chloride, chlorobenzene, and dichloromethane, and mixtures thereof.

When the compound (c-1) is used as the component (C) in the preparation of the preliminary contact solid catalyst component (II), the compound (c-1) is used in such an amount that a mole ratio [(c-1)/(Al(B))] of the compound (c-1) to aluminum atoms (Al(B)) in (B) the organoaluminum oxy-compound (b-2) and the optionally used organoaluminum compound (b-1) included in the solid catalyst component (I) is usually 0.001 to 2, and preferably 0.002 to 1.

When the compound (c-2) is used as the component (C), the compound (c-2) is used in such an amount that an atomic ratio [(Al(c-2))/(Al(B))] of aluminum atoms (Al(c-2)) in the compound (c-2) to aluminum atoms (Al(B)) in (B) the organoaluminum oxy-compound (b-2) and the optionally used organoaluminum compound (b-1) included in the solid catalyst component (I) is usually 0.001 to 3, and preferably 0.002 to 1.5.

When the compound (c-3) is used as the component (C), the compound (c-3) is used in such an amount that a mole ratio [(c-3)/(Al(B))] of the compound (c-3) to aluminum atoms (Al(B)) in (B) the organoaluminum oxy-compound (b-2) and the optionally used organoaluminum compound (b-1) included in the solid catalyst component (I) is usually 0.002 to 1, and preferably 0.002 to 0.02.

When the preparation of the preliminary contact solid catalyst component (II) uses a plurality of kinds of the components from among the components (c-1) to (c-3), an amount of each of the components to be used satisfies the relationship of the above-described mole ratio of the each component to the aluminum atoms (Al(B)) in the organoaluminum oxy-compound (b-2) and the optionally used organoaluminum compound (b-1).

It is not preferable to use the component (C) in an excessively small amount, since the properties of particles of the polymer component by-produced in the α-olefin production process become hollow, which negatively affects separation and drying processes for the particles. In addition, it is also not preferable to use the compound (C) in an excessively large amount, since catalytic activity is reduced, which is economically disadvantageous.

A temperature of contact of the above-described respective components with each other is usually −50° to 150° C. and preferably −20 to 120° C., and a time length of the contact is 1 to 1000 minutes and preferably 5 to 600 minutes.

In the preliminary contact solid catalyst component (II) thus obtained, (B) the organoaluminum oxy-compound (b-2) and the optionally used organoaluminum compound (b-1) are supported in an amount of usually $10^{-5}$ to $10^{-1}$ mol, and preferably $2 \times 10^{-5}$ to $5 \times 10^{-2}$ mol per gram of the solid carrier (A) in terms of aluminum atom. When the compound (c-1) is used as the component (C), the compound (c-1) is supported in an amount of usually $10^{-8}$ to $2 \times 10^{-1}$ mol, and preferably $2 \times 10^{-8}$ to $10^{-2}$ mol. When the compound (c-2) is used as the component (C), the compound (c-2) is supported in an amount of usually $10^{-8}$ to $3 \times 10^{-1}$ mol, and preferably $2 \times 10^{-8}$ to $1.5 \times 10^{-2}$ mol.

When the compound (c-3) is used as the component (C), the compound (c-3) is supported in an amount of $2 \times 10^{-8}$ to $10^{-1}$ mol, and preferably $2 \times 10^{-8}$ to $2 \times 10^{-7}$ mol.

[Olefin Oligomerization Catalyst (III)]

The olefin oligomerization catalyst (III) according to the present invention is obtained by contacting the above-described preliminary contact solid catalyst component (II) with the transition metal compound (D).

<(D) Transition Metal Compound>

The transition metal compound (D) used in the present invention is a transition metal compound having a transition metal atom selected from Group III to Group X of the periodic table, and preferably Group III to Group VI thereof, which is capable of functioning as an olefin oligomerization catalyst.

Examples of the transition metal compound capable of functioning as the olefin oligomerization catalyst include a compound including a source of chromium, molybdenum, or tungsten and a ligand containing at least one phosphorus, arsenic, or antimony atom bound to at least one hydrocarbyl group described in JP-T-2004-502527, a compound including a chromium compound, a pyrrole-containing compound, and a metalalkyl described in JP-A-6-239920, a tantalum compound described in JP-A-2005-152889, a titanium compound described in JP-T-2004-524959, a compound prepared from a chromium compound and a heteroatom ligand described in each of JP-T-2006-516265 and JP-T-2006-517528, a zirconium compound described in JP-A-H6-32745, a chromium compound, a titanium compound, a zirconium compound, a hafnium compound, and a tantalum compound described in Chemical Reviews, 2011, vol. 111, pp. 2321 to 2341, and a titanium compound described in WO 2009/5003.

The present inventors think that a particularly important point of means for achieving the above-described objective to be achieved by the present invention: "to provide an olefin oligomerization catalyst that allows properties of particles of a polymer component by-produced in an α-olefin production process to be obtained in such a shape that does not negatively affect a separation process for the particles" is to obtain the above-described preliminary contact solid catalyst component (II). Accordingly, in obtaining the advantageous effect of the invention, any compound, including those exemplified above, can be used as the transition metal compound (D) as long as the compound is a transition metal compound having olefin oligomerization ability, that is, a transition metal compound capable of functioning as an olefin oligomerization catalyst.

Among the transition metal compounds mentioned above, compounds represented by general formula (1) below are preferably used from the viewpoint of high catalytic activity and high selectivity of an α-olefin to be obtained.

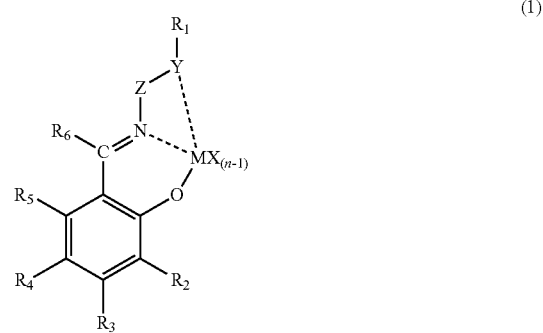

(1)

In the general formula (1), $R^1$ and $R^6$ may be the same as or different from each other and each represent a hydrogen atom, a halogen atom, a hydrocarbon atom, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group, or a tin-containing group, in which two or more of $R^1$ to $R^6$ may be linked to each other. In addition, $R^1$ may be linked to Z.

Examples of the halogen atom include fluorine, chlorine, bromine, and iodine.

Examples of the hydrocarbon group include linear or branched alkyl groups having 1 to 30, preferably 1 to 20, and more preferably 1 to 10 carbon atoms, such as a methyl group, an ethyl group, an n-propyl group, an isopropyl group, an n-butyl group, an isobutyl group, a sec-butyl group, a tert-butyl group, a neopentyl group, and an n-hexyl group; linear or branched alkenyl groups having 2 to 30, and preferably 2 to 20 carbon atoms, such as a vinyl group, an allyl group, and an isopropenyl group; linear or branched alkynyl groups having 2 to 30, and preferably 2 to 20 carbon atoms, such as an ethynyl group and a propargyl group; cyclic saturated hydrocarbon groups having 3 to 30, and preferably 3 to 20 carbon atoms, such as a cyclopropyl group, a cyclobutyl group, a cyclopentyl group, a cyclohexyl group, and an adamantyl group; cyclic unsaturated hydrocarbon groups having 5 to 30 carbon atoms, such as a cyclopentadienyl group, an indenyl group, and a fluorenyl group; aryl groups having 6 to 30, and preferably 6 to 20 carbon atoms, such as a phenyl group, a naphthyl group, a biphenyl group, a terphenyl group, a phenanthryl group, and an anthracenyl group; alkyl-substituted aryl groups such as a tolyl group, an isopropylphenyl group, a t-butylphenyl group, a dimethylphenyl group, and a di-t-butylphenyl group; and alkylidene groups having 1 to 30, and preferably 5 to 10 carbon atoms, such as a benzylidene group, a methylidene group, and an ethylidene group.

The hydrocarbon groups may have at least one hydrogen atom substituted by halogen. Examples of such halogenated hydrocarbon groups include halogenated hydrocarbon groups having 1 to 30, and preferably 1 to 20 carbon atoms, such as a trifluoromethyl group, a pentafluorophenyl group, and a chlorophenyl group.

In addition, the hydrocarbon groups may have hydrogen atoms substituted by other hydrocarbon groups, and examples of such hydrocarbon groups include aryl-substituted alkyl groups such as a benzyl group, a cumyl group, a diphenylethyl group, and a trityl group.

Furthermore, the hydrocarbon groups may be those linked to heterocyclic compound residues, oxygen-containing groups, nitrogen-containing groups, sulfur-containing groups, phosphorus-containing groups, boron-containing groups, silicon-containing groups, germanium-containing groups, or tin-containing groups, which will be described later.

Among these hydrocarbon groups, preferred are linear or branched alkyl groups having 1 to 30, preferably 1 to 20, more preferably 1 to 10, and still more preferably 2 to 10 carbon atoms, such as a methyl group, an ethyl group, an n-propyl group, an isopropyl group, an n-butyl group, an isobutyl group, a sec-butyl group, a t-butyl group, a neopentyl group, an n-hexyl group, and an adamantyl group; cyclic saturated hydrocarbon groups having 3 to 30, and preferably 3 to 20 carbon atoms, such as a cyclopropyl group, a cyclobutyl group, a cyclopentyl group, a cyclohexyl group, and an adamantyl group; aryl groups having 6 to 30, and preferably 6 to 20 carbon atoms, such as a phenyl group, a naphthyl group, a biphenyl group, a terphenyl group, a phenanthryl group, and an anthracenyl group; substituted aryl groups in which the above-mentioned aryl groups have been substituted by 1 to 5 substituents such as a halogen atom, an alkyl group or an alkoxy group having 1 to 30, and preferably 1 to 20 carbon atoms, and an aryl group or an aryloxy group having 6 to 30, and preferably 6 to 20 carbon atoms.

Examples of the heterocyclic compound residue include nitrogen-containing compounds such as pyrrole, pyridine, pyrimidine, quinolone, and triazine; oxygen-containing compounds such as furan and pyran; and sulfur-containing compounds such as thiophene. The above heterocyclic compound residues may have hydrogen atoms, for example, substituted by substituents such as alkyl groups having 1 to 30, and preferably 1 to 20 carbon atoms and alkoxy groups having 1 to 30, and preferably 1 to 20 carbon atoms.

Examples of the oxygen-containing groups include alkoxy groups, aryloxy groups, ester groups, ether groups, acyl groups, carboxyl groups, carbonate groups, hydroxyl groups, peroxy groups, and carboxylic anhydride groups.

Examples of the nitrogen-containing groups include amino groups, alkylamino groups, arylamino groups, alkylarylamino groups, imino groups, alkylimino groups, arylimino groups, imide groups, substituted imide groups, amide groups, substituted amide groups, hydrazino groups, hydrazono groups, nitro groups, nitroso groups, cyano groups, isocyano groups, cyanate groups, amidino groups, diazo groups, and ammonium salts of amino groups, alkylamino groups, arylamino groups, or alkylarylamino groups.

The alkylamino groups are preferably dimethylamino groups and ethylmethylamino groups. The arylamino groups are preferably diphenylamino groups. The alkylimino groups are preferably methylimino groups, ethylimino groups, propylimino groups, and butylimino groups. The arylimino groups are preferably phenylimino groups. The substituted imide groups are preferably acetimide groups and benzimide groups. The substituted amide groups are preferably acetamide groups, N-methylacetamide groups, and N-methylbenzamide groups.

Examples of the sulfur-containing groups include mercapto groups, thioester groups, dithioester groups, alkylthio groups, arylthio groups, thioacyl groups, thioether groups, thiocyanate groups, isothiocyanate groups, sulfonate groups, sulfonamide groups, thiocarboxyl group, dithiocarboxyl groups, sulfo groups, sulfonyl groups, sulfinyl groups, and sulfenyl groups.

The alkylthio groups are preferably methylthio groups and ethylthio groups. The arylthio groups are preferably phenylthio groups, methylphenylthio groups, and naphthylthio groups. The thioester groups are preferably acetylthio groups, benzoylthio groups, methylthiocarbonyl groups, and phenylthiocarbonyl groups. The sulfonate groups are preferably methyl sulfonate groups, ethyl sulfonate groups, and phenyl sulfonate groups. The sulfonamide groups are preferably phenylsulfonamide groups, N-methylsulfonamide groups, and N-methyl-p-toluenesulfonamide.

Examples of the phosphorus-containing groups include phosphide groups, phosphoryl groups, thiophosphoryl groups, and phosphate groups.

Examples of the boron-containing groups include boranediyl groups, boranetriyl groups, diboranyl groups, alkyl-substituted boron groups, aryl-substituted boron groups, halogenated boron groups, and alkyl-substituted halogenated boron groups.

Examples of the alkyl-substituted boron groups include $(Et)_2B$—, $(iPr)_2B$—, $(iBu)_2B$—, $(Et)_3B$, $(iPr)_3B$, and $(iBu)_3B$. Examples of the aryl-substituted boron groups include $(C_6H_5)_2B$—, $(C_6H_5)_3B$, $(C_6F_5)_3B$, and $(3,5\text{-}(CF_3)_2C_6H_3)_3B$. Examples of the halogenated boron groups include $BCl_2$— and $BCl_3$. Examples of the alkyl-substituted halogenated boron groups include $(Et)BCl$—, $(iBu)BCl$—, and $(C_6H_5)_2BCl$. Among these groups, those in which three groups are linked to boron may be in a state of coordination bond. Herein, Et represents an ethyl group, iPr represents an isopropyl group, and iBu represents an isobutyl group.

Examples of the aluminum-containing groups include alkyl-substituted aluminum groups, aryl-substituted aluminum groups, halogenated aluminum groups, and alkyl-substituted halogenated aluminum groups.

Examples of the alkyl-substituted aluminum groups include $(Et)_2Al—$, $(iPr)_2Al—$, $(iBu)_2Al—$, $(Et)_3Al$, $(iPr)_3Al$, and $(iBu)_3Al$. Examples of the aryl-substituted aluminum groups include $(C_6H_5)_2Al—$. Examples of the halogenated aluminum groups include $AlCl_2—$ and $AlCl_3$. Examples of the alkyl-substituted halogenated aluminum groups include $(Et)AlCl—$ and $(iBu)AlCl—$. Among these groups, those in which three groups are linked to aluminum may be in a state of coordination bond. Herein, Et represents an ethyl group, iPr represents an isopropyl group, and iBu represents an isobutyl group.

Examples of the silicon-containing groups include silyl groups, siloxy groups, hydrocarbon-substituted silyl groups, and hydrocarbon-substituted siloxy groups.

Examples of the hydrocarbon-substituted silyl groups include methylsilyl groups, dimethylsilylgroups, trimethylsilyl groups, ethylsilyl groups, diethylsilyl groups, triethylsilyl groups, diphenylmethylsilyl groups, triphenylsilyl groups, dimethylphenylsilyl groups, dimethyl-t-butylsilyl groups, and dimethyl(pentafluorophenyl)silyl groups. Among the hydrocarbon-substituted silyl groups, preferred are methylsilyl groups, dimethylsilyl groups, trimethylsilyl groups, ethylsilyl groups, diethylsilyl groups, triethylsilyl groups, dimethylphenylsilyl groups, and triphenylsilyl groups, and particularly preferred are trimethylsilyl groups, triethylsilyl groups, triphenylsilyl groups, and dimethylphenylsilyl groups. Specific examples of the hydrocarbon-substituted siloxy groups include trimethylsiloxy groups.

Examples of the germanium-containing groups include groups in which silicon of the silicon-containing groups are substituted by germanium. In addition, examples of the tin-containing groups include groups in which silicon of the silicon-containing groups are substituted by tin.

Two or more of $R^1$ to $R^6$ may be linked to each other. Preferably, adjacent groups among $R^1$ to $R^6$ may be linked to each other to form an aliphatic ring, an aromatic ring, or a hydrocarbon ring including a heteroatom such as a nitrogen atom, and these rings may further contain any substituent.

Additionally, $R^1$ may be linked to Z. When $R^1$ is linked to Z, the linkage of $R^1$ to Z may form an aliphatic ring, an aromatic ring, or a hydrocarbon ring including a heteroatom such as a nitrogen atom, and these rings may further contain any substituent.

The above-described $R^1$ to $R^6$ each are preferably a hydrogen atom, a halogen atom, a hydrocarbon group whose hydrogen atom may be substituted by a halogen atom, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amide group, an imide group, an amino group, an imino group, a sulfonate group, a sulfonamide group, a cyano group, a nitro group, a carboxyl group, a sulfo group, a mercapto group, an aluminum-containing group, or a hydroxy group.

The above-described $R^1$ preferably represents a methyl group, an ethyl group, or an isopropyl group, and particularly preferably represents a methyl group.

The above-described $R^2$ preferably represents a phenyl group, an α-cumyl group, a tert-butyl group, or a 1-adamantyl group, and particularly preferably represents a 1-adamantyl group.

The above-described $R^4$ preferably represents a methyl group, a cyclohexyl group, a tert-butyl group, or a 1-adamantyl group, and particularly preferably represents a methyl group.

In the above general formula (1), M represents a transition metal atom selected from Group III to Group X of the periodic table; and n represents a valence of M.

Preferable examples of the above M include transition metal atoms of Group III of the periodic table, such as yttrium, scandium, lanthanum; transition metal atoms of Group IV of the periodic table, such as titanium, zirconium, and hafnium; transition metal atoms of Group V of the periodic table, such as vanadium and tantalum; transition metal atoms of Group VI of the periodic table, such as chromium; transition metal atoms of Group VIII of the periodic table, such as iron; transition metal atoms of Group IX of the periodic table, such as cobalt; transition metal atoms of Group X of the periodic table, such as nickel; and transition metal atoms of Group XI of the periodic table, such as copper. Among the examples of M, more preferred are transition metal atoms of Group IV of the periodic table, more preferred are titanium, zirconium, and hafnium, and particularly preferred is titanium.

n represents a valence corresponding to a transition metal atom M. When the transition metal atom M is yttrium, scandium, or lanthanum, n usually represents 3. When the transition metal atom M is any one of the transition metal atoms of Group IV of the periodic table, such as titanium, zirconium, and hafnium, n usually represents 4. When the transition metal atom M is vanadium or tantalum, n usually represents 3 to 5. When the transition metal atom M is chromium, n usually represents 3. When the transition metal atom M is cobalt, iron, nickel, or copper, n usually represents 2.

In the general formula (1), X represents a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group, or a tin-containing group. Atoms and groups represented by X may be the same as or different from each other. In addition, the groups represented by X may be linked to each other to form a ring.

Herein, the halogen atom usually represents fluorine, chlorine, bromine, or iodine.

Examples of the hydrocarbon group include the same ones as those exemplified for the $R^1$ to $R^6$ of the general formula (1).

Examples of the hydrocarbon group include alkyl groups such as methyl groups, ethyl groups, propyl groups, butyl groups, hexyl groups, octyl groups, nonyl groups, dodecyl groups, and eicosyl groups; cyclic saturated hydrocarbon groups having 3 to 30 carbon atoms, such as cyclopentyl groups, cyclohexyl groups, norbornyl groups, and adamantyl groups; alkenyl groups such as vinyl groups, propenyl groups, and cyclohexenyl groups; arylalkyl groups such as benzyl groups, phenylethyl groups, and phenylpropyl groups; aryl groups such as phenyl groups, tolyl groups, dimethylphenyl groups, trimethylphenyl groups, ethylphenyl groups, propylphenyl groups, biphenyl groups, naphthyl groups, methylnaphthyl groups, anthryl groups, and phenanthryl groups.

The hydrocarbon groups may have at least one hydrogen atom substituted by halogen. As such halogenated hydrocarbon groups, preferred are halogenated hydrocarbon groups having 1 to 30 carbon atoms, and more preferred are halogenated hydrocarbon groups having 1 to 20 carbon atoms.

Examples of the heterocyclic compound residue include the same ones as those exemplified for the $R^1$ to $R^6$ of the general formula (1).

Examples of the oxygen-containing group include the same ones as those exemplified for the $R^1$ to $R^6$ of the general formula (1). Examples of the oxygen-containing group include hydroxy groups; alkoxy groups such as methoxy groups, ethoxy groups, propoxy groups, and butoxy groups; aryloxy groups such as phenoxy groups, methylphenoxy groups, dimethylphenoxy groups, and naphthoxy groups; arylalkoxy groups such as phenylmethoxy groups and phenylethoxy groups; acetoxy groups; and carbonyl groups.

Examples of the sulfur-containing group include the same ones as those exemplified for the $R^1$ to $R^6$ of the general formula (1). Examples of the sulfur-containing group include sulfonate groups such as methyl sulfonate groups, trifluoromethane sulfonate groups, phenylsulfonate groups, benzylsulfonate groups, p-toluenesulfonate groups, trimethylbenzensulfonate groups, triisobutyl benzensulfonate groups, p-chlorobenzensulfonate group, and pentafluorobenzensulfonate groups; sulfinate groups such as methyl sulfinate groups, phenylsulfinate groups, benzylsulfinate groups, p-toluenesulfinate groups, trimethylbenzensulfinate groups, and pentafluorobenzensulfinate groups; alkylthio groups; and arylthio groups.

Examples of the nitrogen-containing groups include the same ones as those exemplified for the $R^1$ to $R^6$ of the general formula (1). Examples of the nitrogen-containing groups include amino groups; alkylamino groups such as methylamino groups, dimethylamino groups, diethylamino groups, dipropylamino groups, dibutylamino groups, and dicyclohexylamino groups; arylamino groups such as phenylamino groups, diphenylamino groups, ditolylamino groups, dinaphtylamino groups, and methylphenylamino groups, and alkylarylamino groups.

Examples of the boron-containing groups include $BR_4$ other than tetraphenyl borate (R represents hydrogen, an alkyl group, an aryl group that may have a substituent, a halogen atom, or the like).

Examples of the phosphorus-containing groups include trialkylphosphine groups such as trimethylphosphine, tributylphosphine, and tricyclohexylphosphine; triarylphosphine groups such as triphenylphosphine and tritolylphosphine; phosphite groups (phosphide groups) such as methyl phosphite, ethyl phosphite, and phenyl phosphite; phosphonic acid groups; and phosphinic acid groups.

Examples of the silicon-containing groups include the same ones as those exemplified for the $R^1$ to $R^6$ of the general formula (1). Examples of the silicon-containing groups include hydrocarbon-substituted silyl groups such as phenylsilyl, diphenylsilyl, trimethylsilyl, triethylsilyl, tripropylsilyl, tricyclohexylsilyl, triphenylsilyl, methyldiphenylsilyl, tritolylsilyl, and trinaphthylsilyl; hydrocarbon-substituted silyl ether groups such as trimethylsilyl ether; silicon-substituted alkyl groups such as trimethylsilylmethyl; and silicon-substituted aryl groups such as trimethylsilylphenyl.

Examples of the germanium-containing groups include the same ones as those exemplified for the $R^1$ to $R^6$ of the general formula (1). Examples of the germanium-containing groups include those in which silicon atoms of the silicon-containing groups are substituted by germanium.

Examples of the tin-containing groups include the same ones as those exemplified for the $R^1$ to $R^6$ of the general formula (1). Examples of the tin-containing groups include those in which silicon atoms of the silicon-containing groups are substituted by tin.

Examples of the halogen-containing groups include fluorine-containing groups such as $PF_6$ and $BF_4$; chlorine-containing groups such as $ClO_4$ and $SbCl_6$; and iodine-containing groups such as $IO_4$.

Examples of the aluminum-containing group include $AlR_4$ (R represents hydrogen, an alkyl group, an aryl group that may have a substituent, a halogen atom, or the like).

Among the atoms and groups represented by X, preferred are halogen atoms and alkyl groups, and more preferred are chlorine, bromine, and methyl groups.

In the general formula (1), Y represents an oxygen atom, a nitrogen atom, a phosphorus atom, or a sulfur atom, which is an atom that forms an ether structure, a ketone structure, an amine structure, an imine structure, or the like.

In the general formula (1), Z represents a hydrocarbon group or a heterocyclic compound residue that may have a substituent, and the minimum number of bonds linking Y and N is 4 to 6.

The presence of the 4 to 6 minimum bonds linking Y and N allows 1-hexene to be produced with high selectivity in ethylene oligomerization reaction performed using the olefin oligomerization catalyst including the transition metal compound (D). In addition, the minimum number of the bonds linking Y and N is preferably 5 or 6, since 1-hexene can be produced with higher selectivity.

When the minimum number of the bonds linking Y and N is 3 or less, the distance between N and Y cannot be sufficiently maintained, and the catalyst becomes an ethylene polymerization catalyst, that is, an olefin polymerization catalyst, for example, as in compounds described in WO/01/44324, Organometallics, 2004, vol. 23, pp. 1684-1688, and Organometallics 2006, vol. 25, pp. 3259-3266. It is thus difficult to obtain suitably an olefin oligomer of 1-hexene or the like.

In addition, when the minimum number of bonds linking Y and N is 7 or more, Y cannot be coordination-bonded to the metal atom M, and the catalyst becomes an ethylene polymerization catalyst, that is, an olefin polymerization catalyst, for example, as in compounds without Y described in Dalton Transaction, 2005, pp. 561-571, so that it is difficult to obtain suitably an olefin oligomer of 1-hexene or the like.

The minimum number of the bonds linking Y and N can be counted as shown in the following (a) and (b). The minimum numbers thereof are 4 in (a) and 5 in (b), respectively.

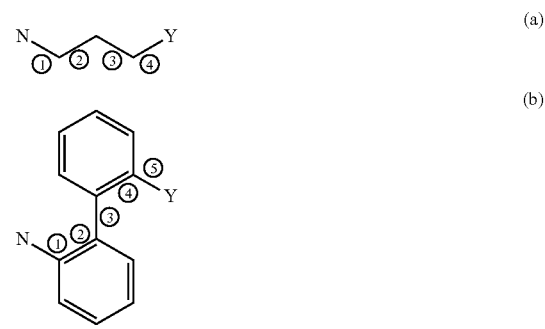

Z represents a group linking N and the above-mentioned Y, and Y, N, and Z preferably form a structure represented by general formula (2):

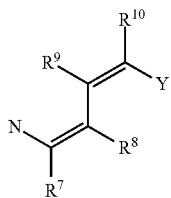
(2)

In the general formula (2), Y represents an oxygen atom, a nitrogen atom, a phosphorus atom, or a sulfur atom.

In addition, $R^7$ to $R^{10}$ may be the same as or different from each other, and each represent a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group, or a tin-containing group, in which when $R^7$ to $R^{10}$ each represent a hydrocarbon group, $R^7$ and $R^8$ may be linked to each other to form a ring, and $R^9$ and $R^{10}$ may be linked to each other to form a ring.

Specific examples of $R^7$ to $R^{10}$ include the same ones as those exemplified for the $R^1$ to $R^6$ of the general formula (1).

Specific examples of the structure formed by Y, N, and Z include those shown in (C) to (H) below, but are not limited thereto. Additionally, in the structures of (C) to (H), hydrogen atoms may be substituted by the groups exemplified for $R^1$ to $R^6$, provided that the structures shown in (C) to (H) include a structure in which $R^1$ is linked to Z.

In the following specific examples, wavy lines connected to a carbon-carbon double bond indicate a cis-isomer or a trans-isomer.

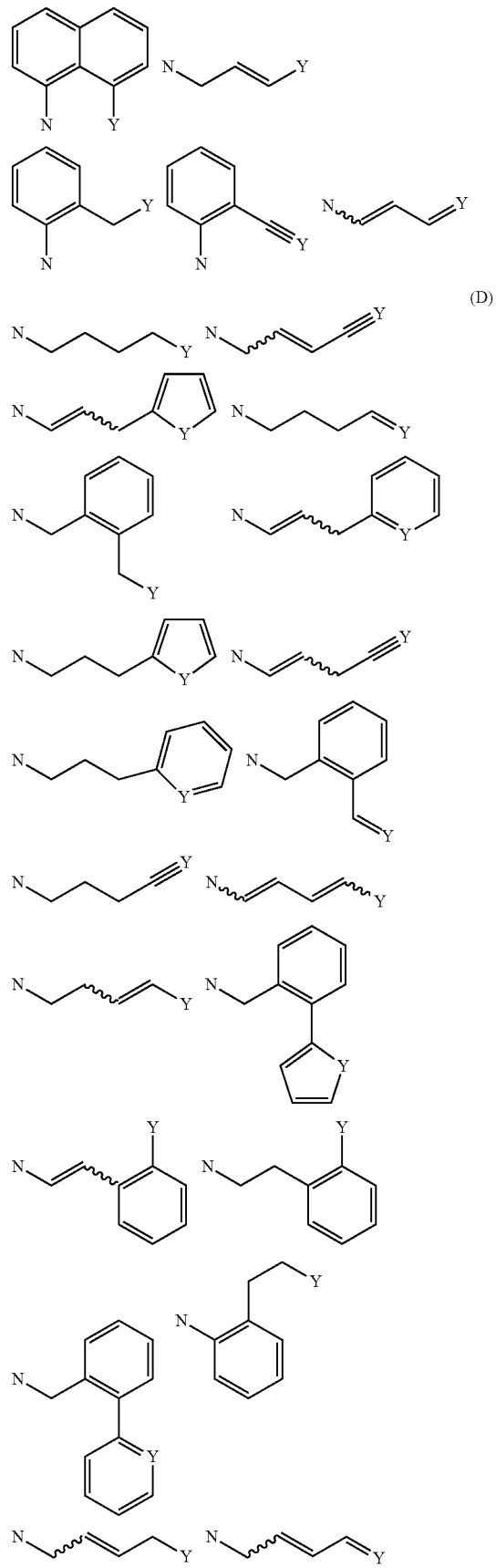

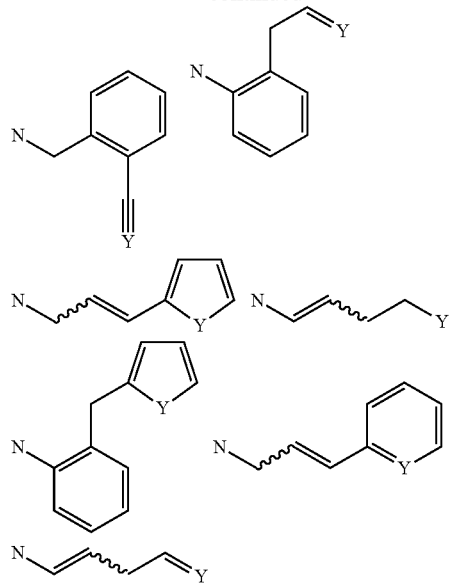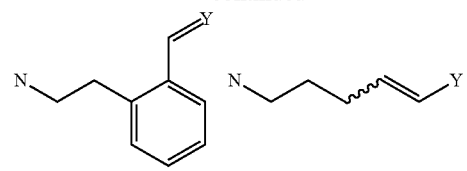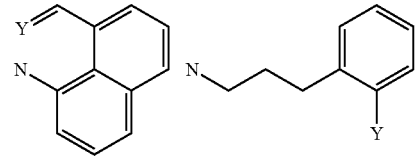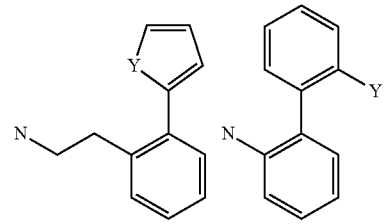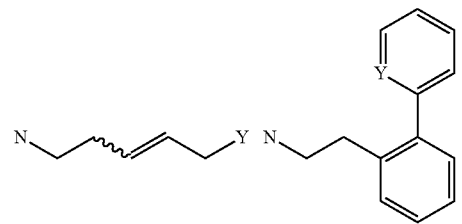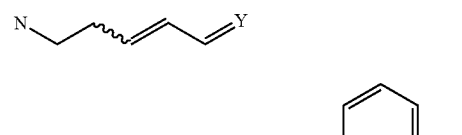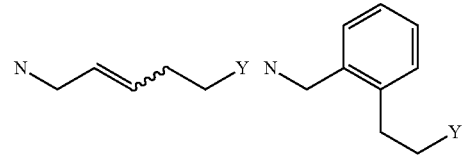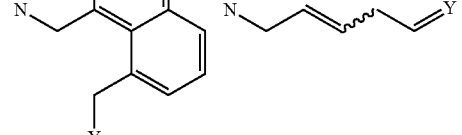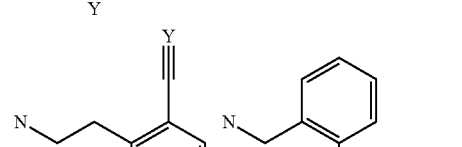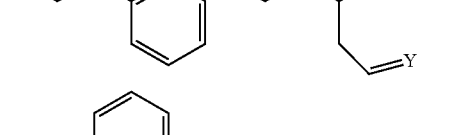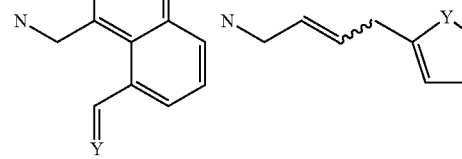

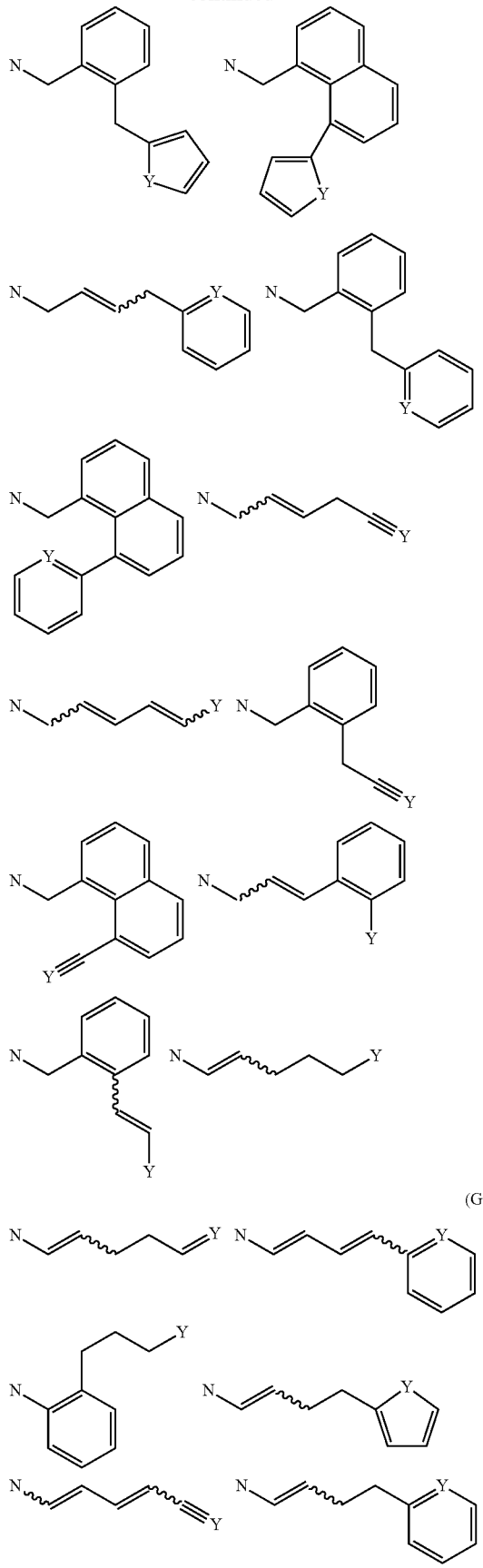
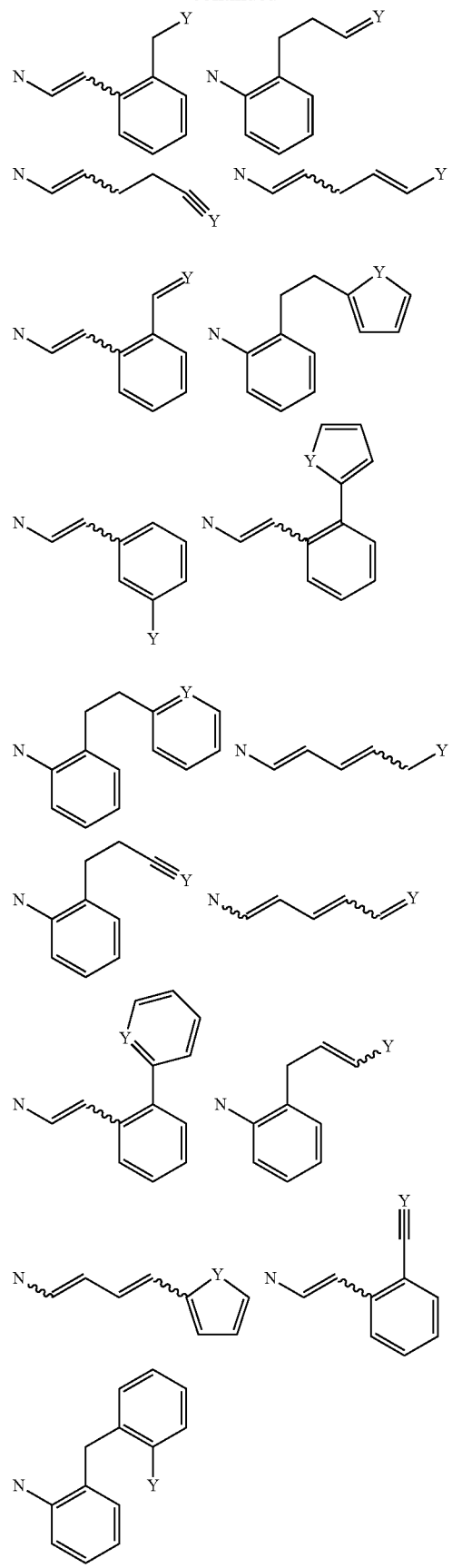

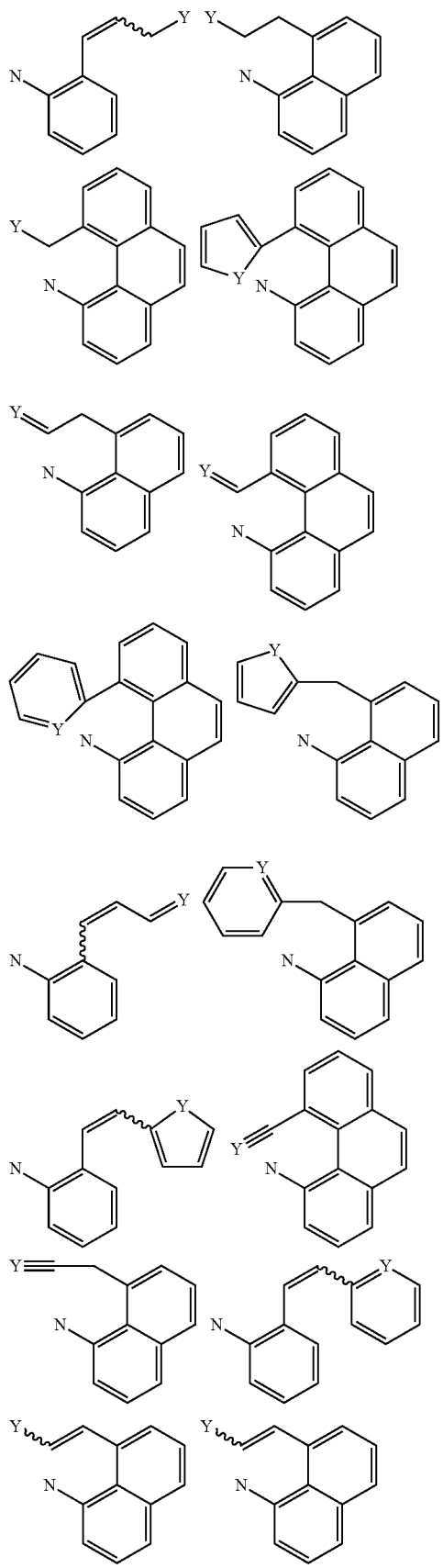

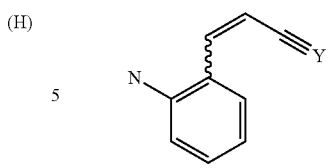

In the above general formula (1), the bond linking Y and Z may be a double bond or a triple bond, and the bond linking Y and $R^1$ may be a double bond or a triple bond. In addition, in the general formula (1), each dotted line represents a coordination bond.

Examples of the compounds represented by the above general formula (1) include compounds represented by chemical formulae below:

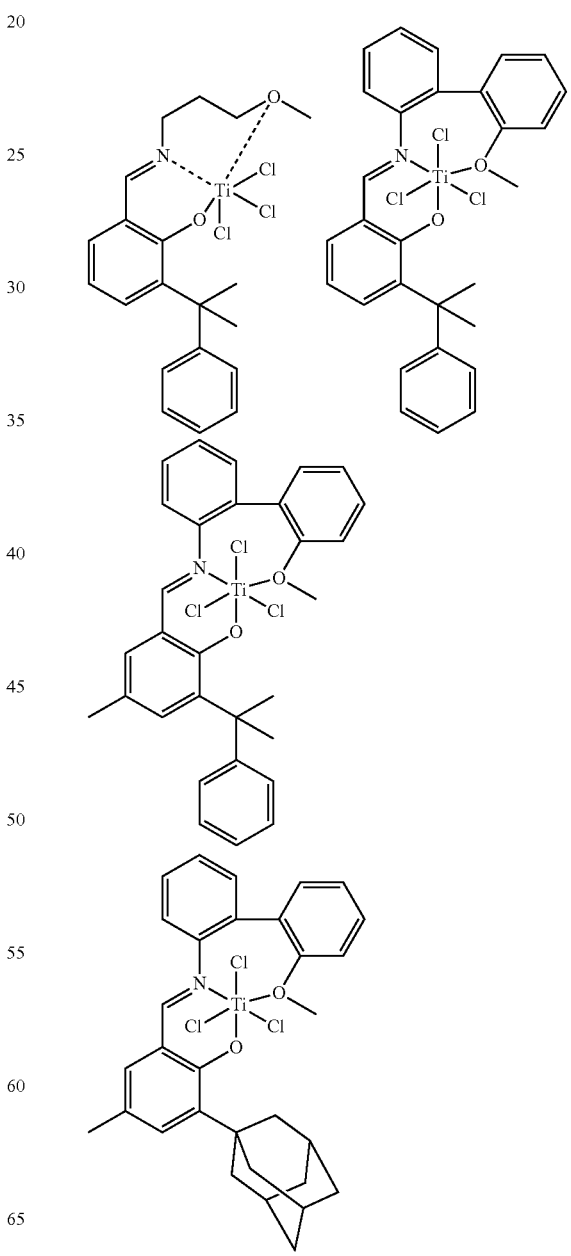

33
-continued
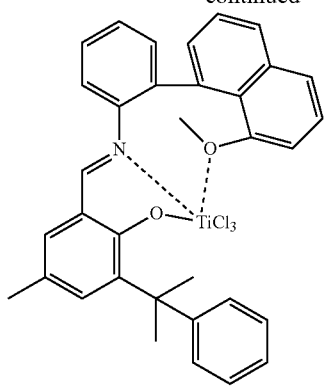
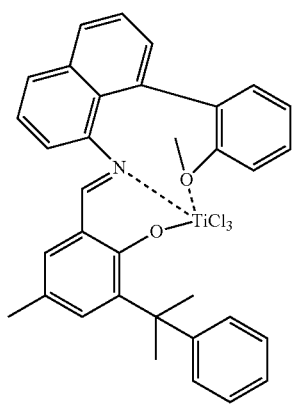
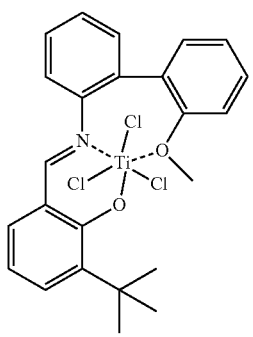
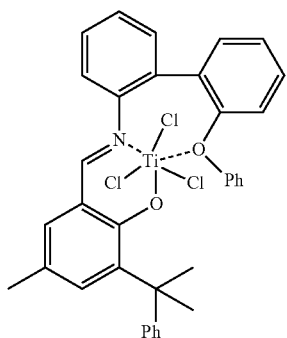
34
-continued
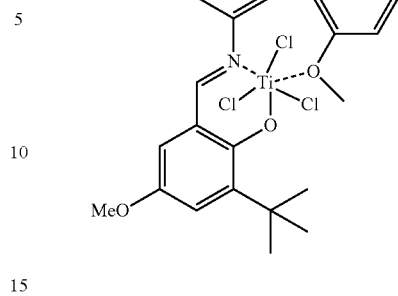
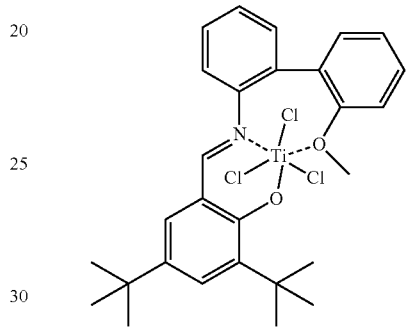
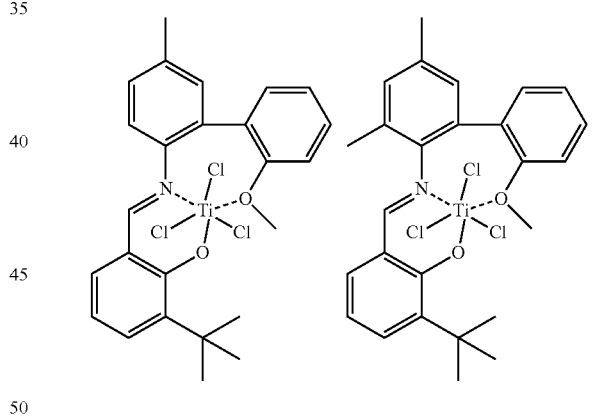
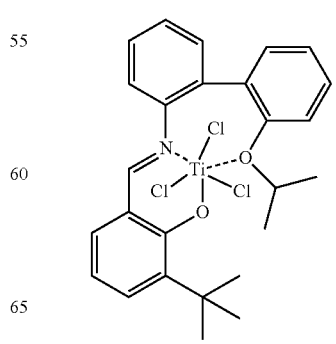

35
-continued
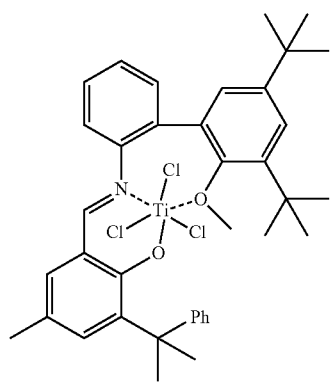
36
-continued
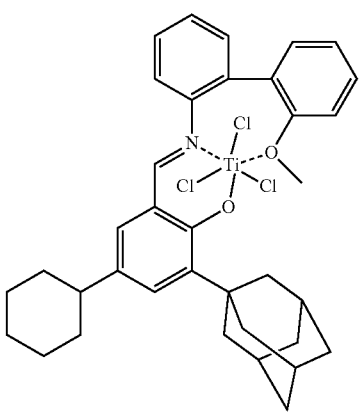
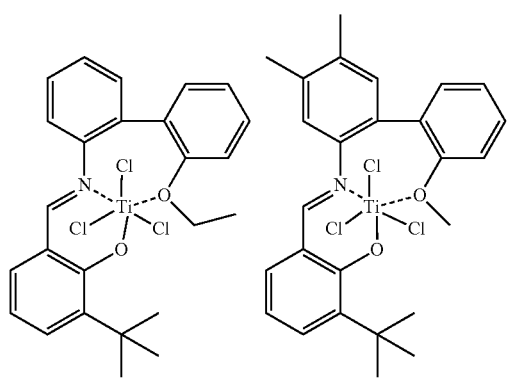
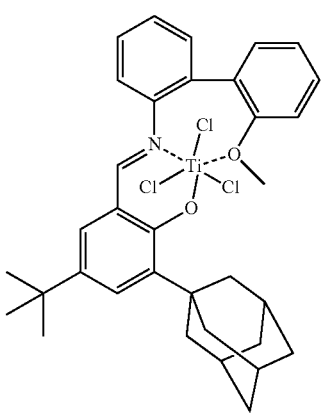
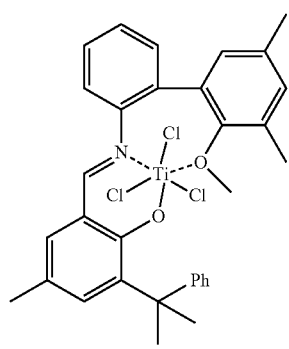
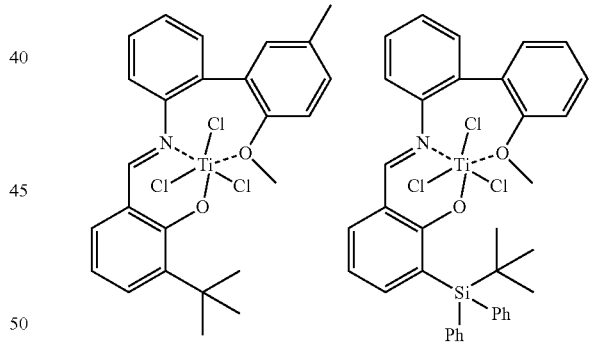
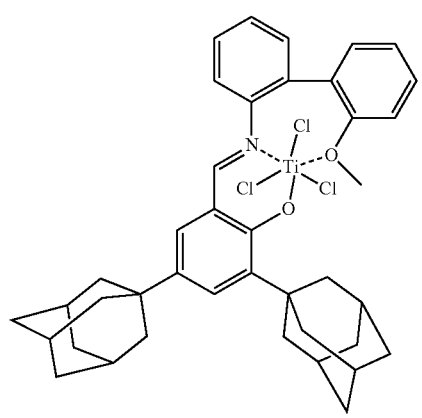
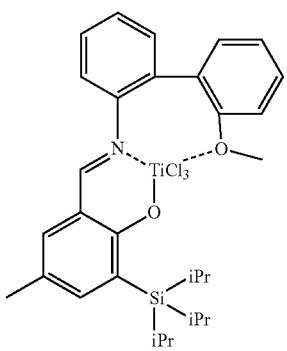

37
-continued
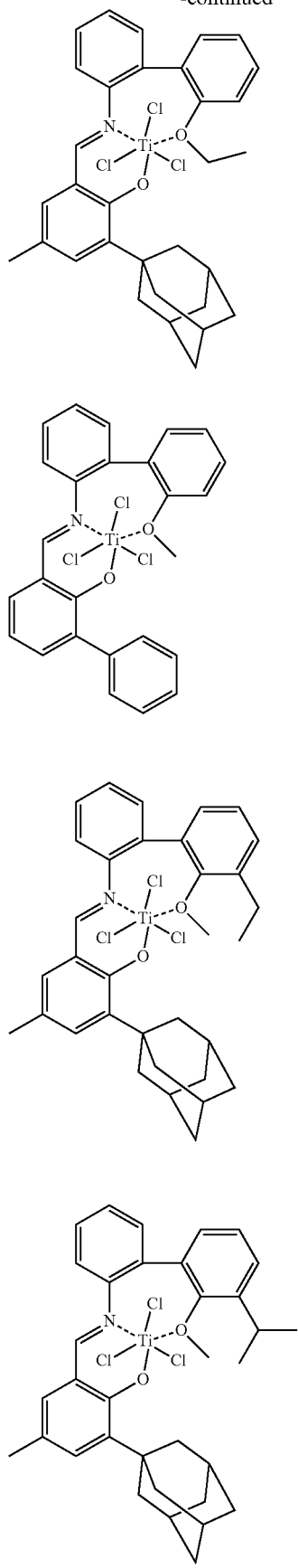
38
-continued
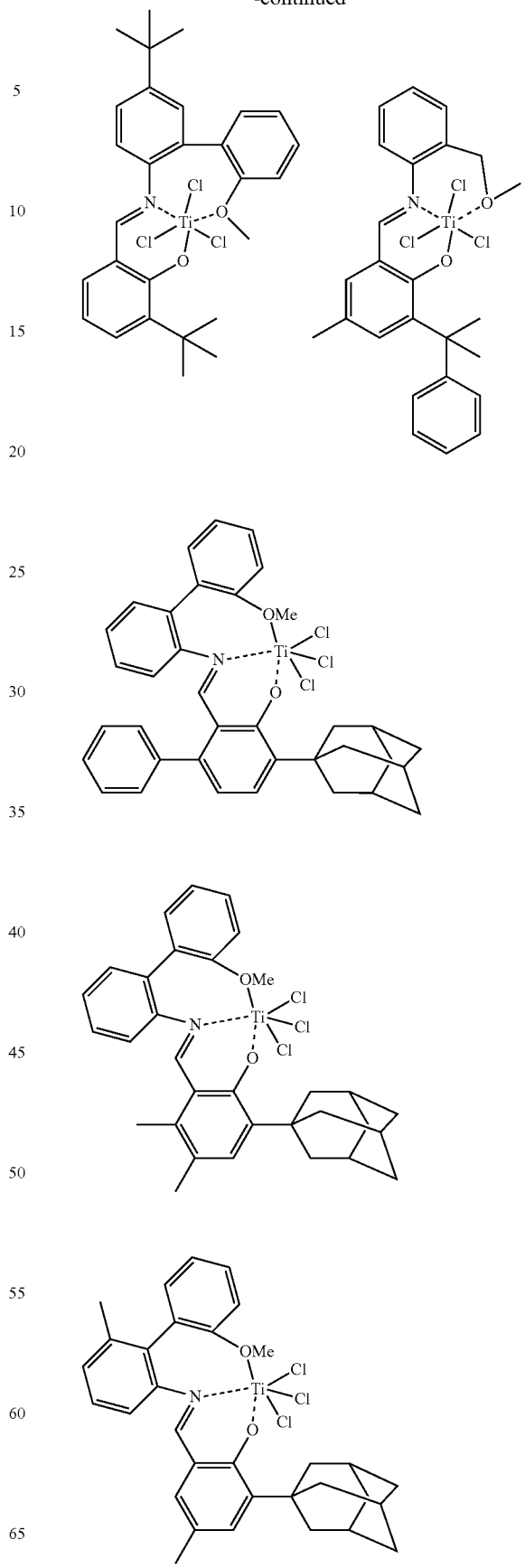

-continued
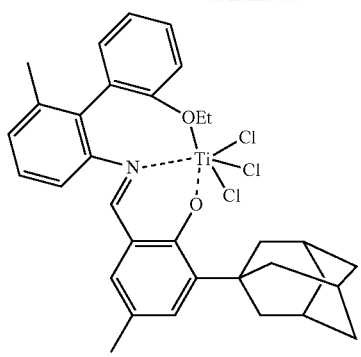
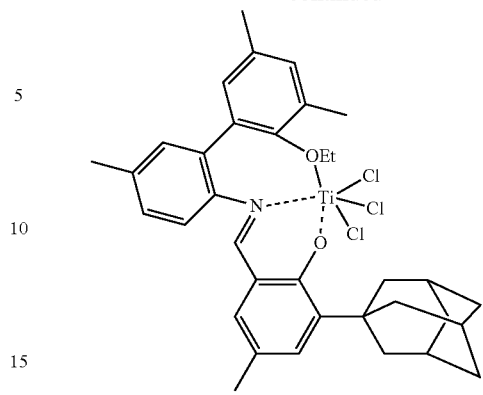
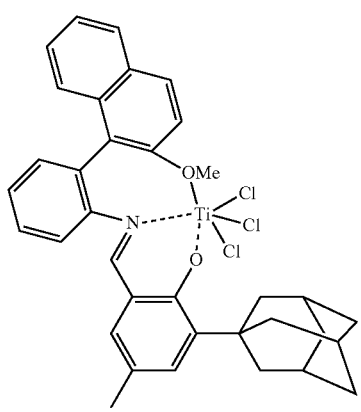
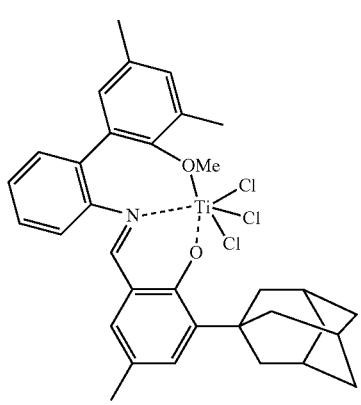
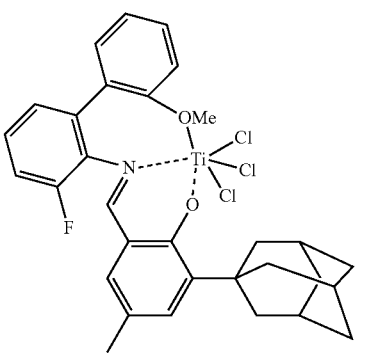

41
-continued
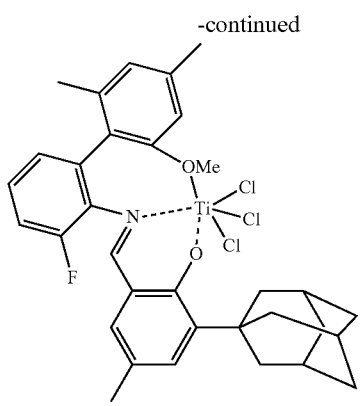
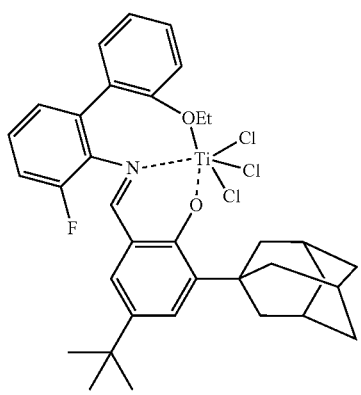
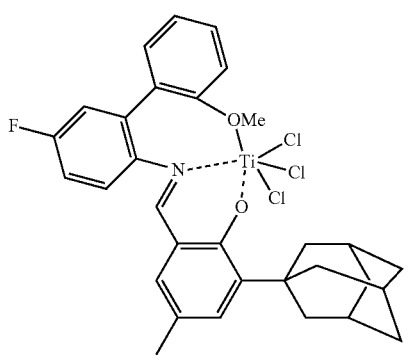
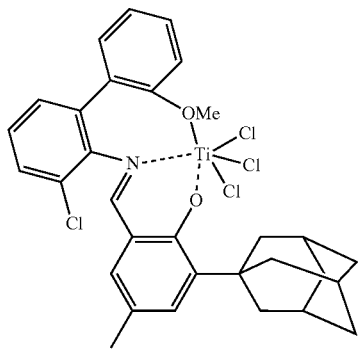
42
-continued
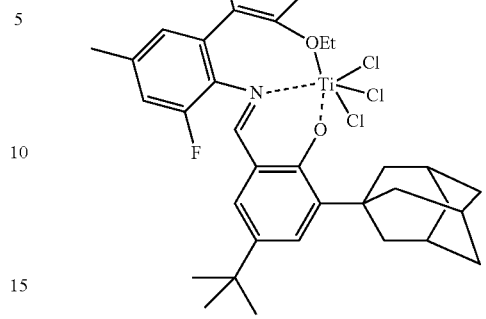
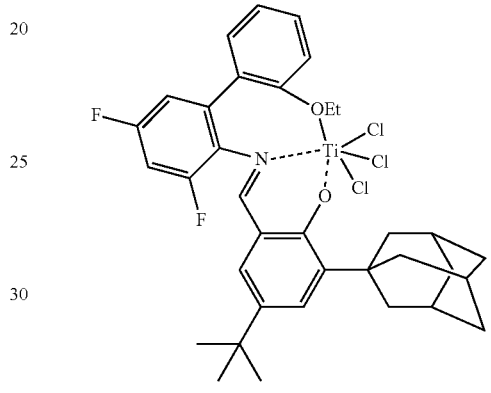
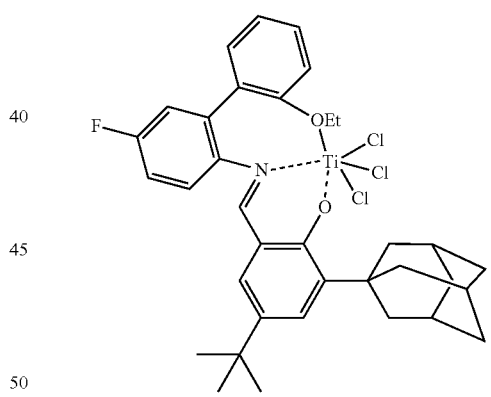
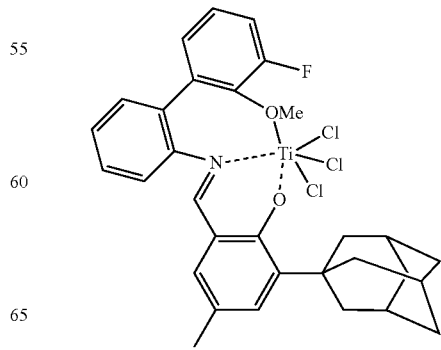

-continued
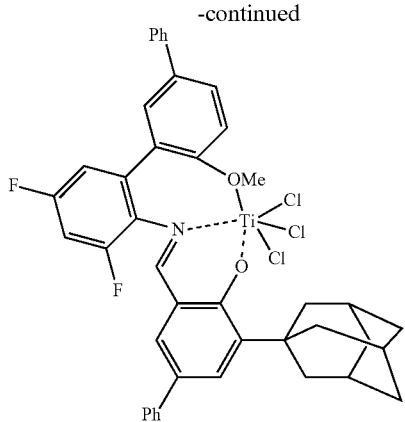
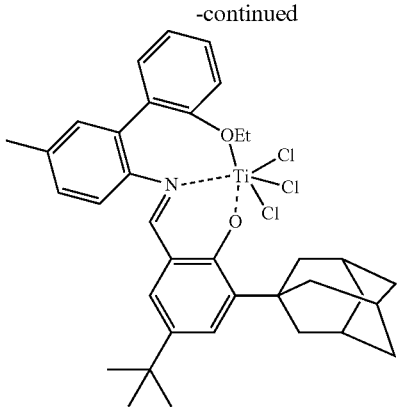
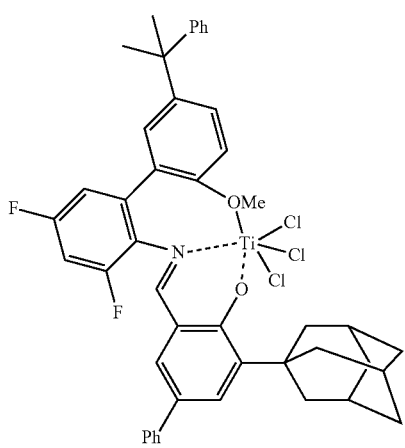
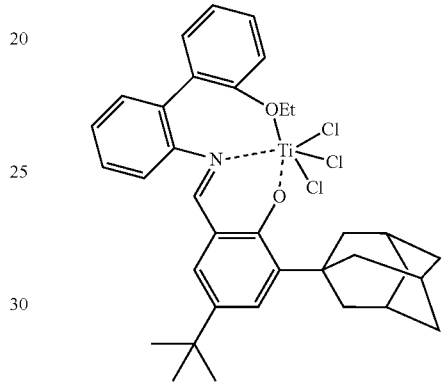
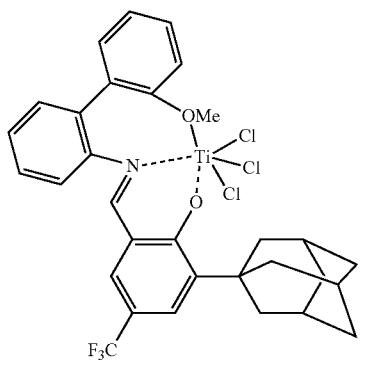
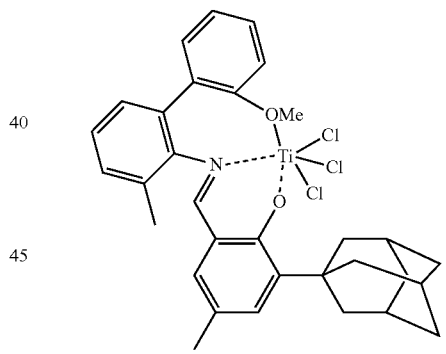
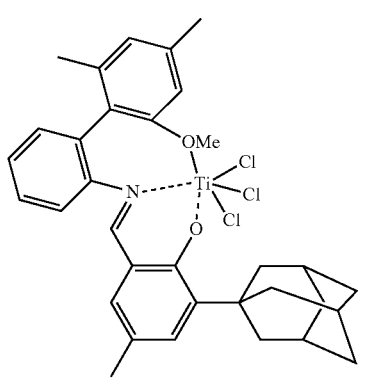
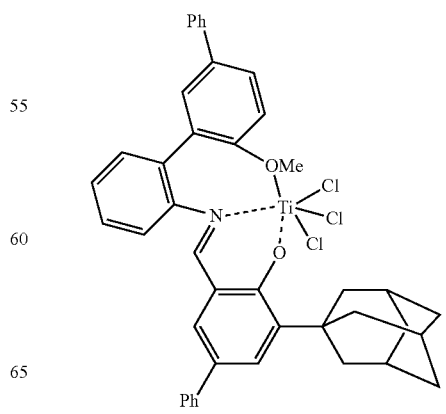

-continued
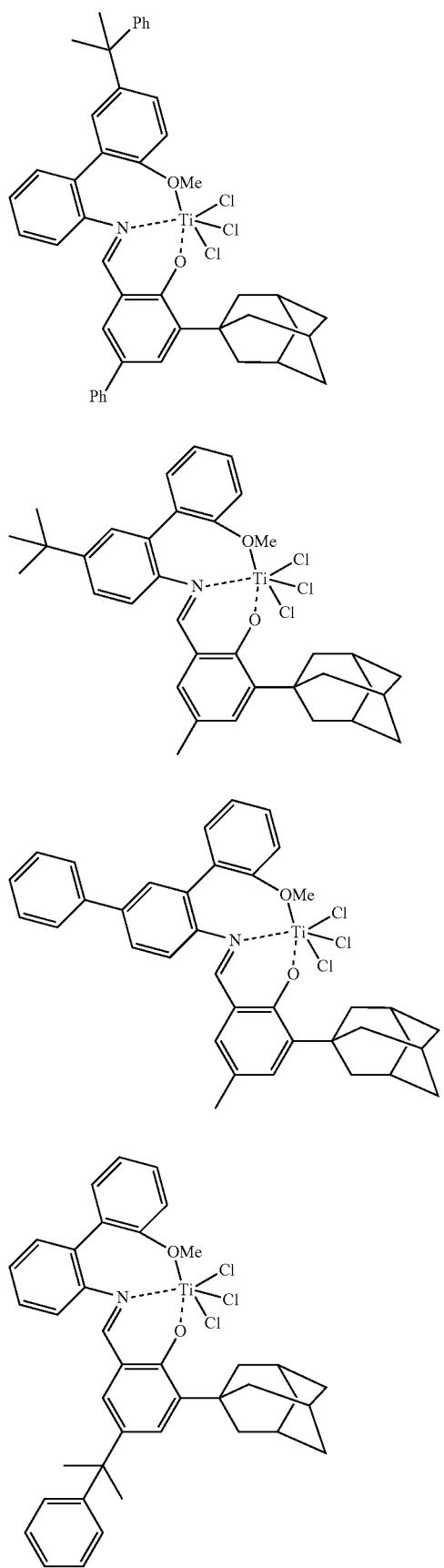
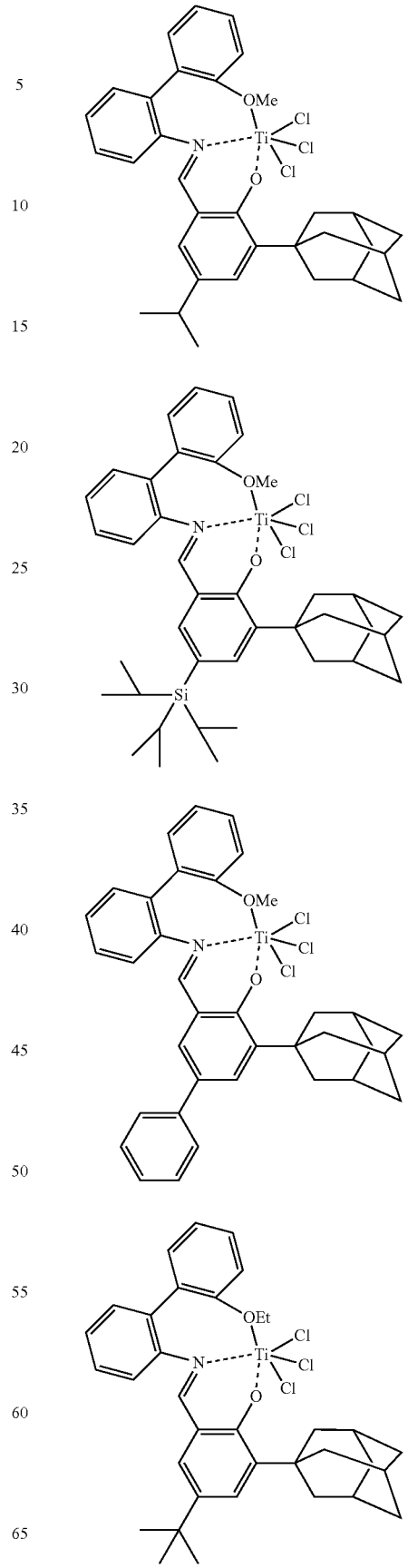

-continued
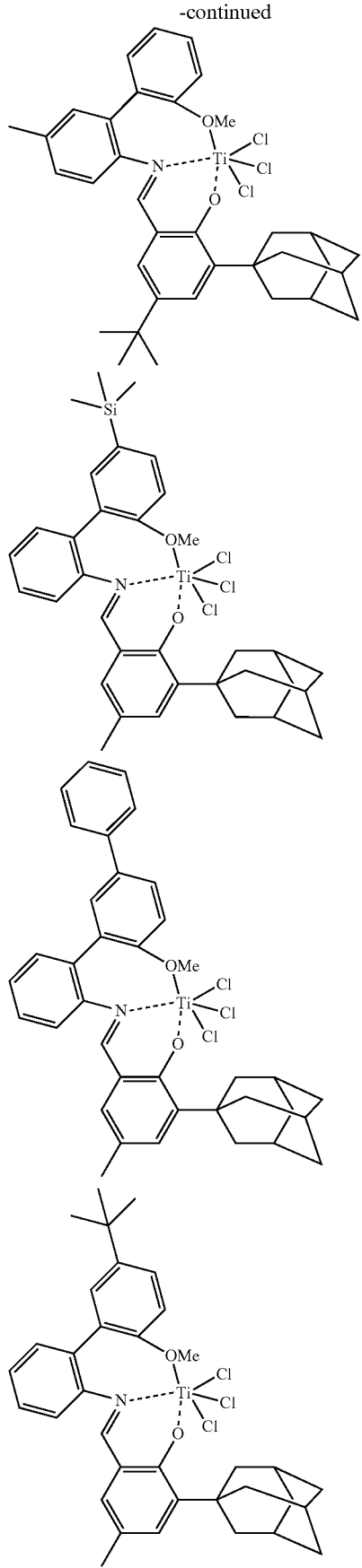
-continued
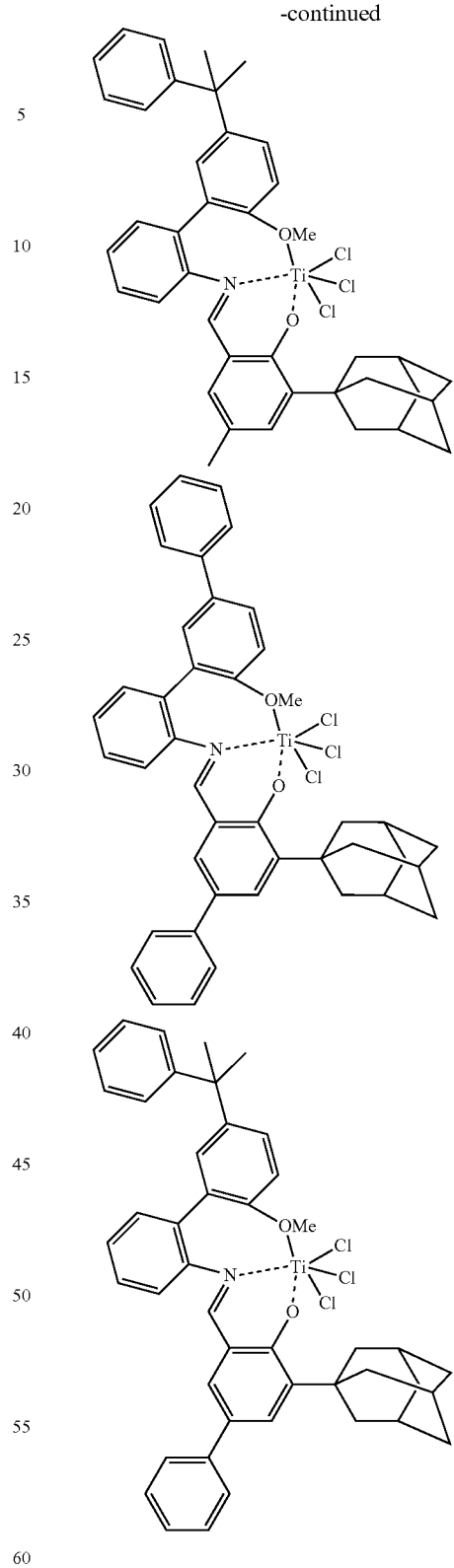
<Method for Preparing Olefin Oligomerization Catalyst (III)>
The olefin oligomerization catalyst (III) according to the present invention can be prepared by contacting the preliminary contact solid catalyst component (II) with the transition metal compound (D).

The preparation of the olefin oligomerization catalyst may use a solvent. The solvent to be used is preferably an organic compound inactive to the preliminary contact solid catalyst component (II) and the transition metal compound (D). Examples of the organic compound include aliphatic hydrocarbons such as propane, butane, hexane, heptane, octane, decane, dodecane, and kerosene; alicyclic hydrocarbons such as cyclopentane, cyclohexane, and methylcyclopentane; aromatic hydrocarbons such as benzene, toluene, and xylene; halogenated hydrocarbons such as ethylene chloride, chlorobenzene, and dichloromethane, and mixtures thereof.

In the preparation of the olefin oligomerization catalyst (III), the transition metal compound (D) is used in an amount of usually 0.005 to 0.5 mmol, and preferably 0.001 to 0.2 mmol per gram of the solid carrier (A) in terms of transition metal atom. Additionally, a mole ratio (Al(B)/M) of aluminum atoms (Al(B)) in the organoaluminum oxy-compound (b-2) and the optionally used organoaluminum compound (b-1) as the component (B) to transition metal atoms (M) in the transition metal compound (D) is usually 10 to 2000, and preferably 100 to 1000.

When an amount of the transition metal compound (D) used is less than 0.005 mmol per gram of the solid carrier (A), it is not preferable since catalytic activity becomes insufficient, which is economically disadvantageous. On the other hand, when the amount of the transition metal compound (D) used is more than 0.5 mmol per gram of the solid carrier (A), it is not preferable since not only catalytic activity per transition metal atom is reduced, but also properties of particles of a polymer component by-produced in an α-olefin production process become hollow, which negatively affects separation and drying processes for the particles.

Additionally, when the mole ratio Al(B)/M is less than 10, it is not preferable since not only catalytic activity per transition metal atom is reduced, but also properties of particles of a polymer component by-produced in an α-olefin production process become hollow, which negatively affects separation and drying processes for the particles. On the other hand, when the mole ratio Al(B)/M is more than 2000, it is not preferable since catalytic activity becomes insufficient, which is economically disadvantageous.

A temperature of contact of the above-described respective components with each other is usually −50 to 150° C., and preferably −20 to 120° C., and a time length of the contact is 1 to 1000 minutes, and preferably 5 to 600 minutes.

In the olefin oligomerization catalyst (III) thus obtained, (B) the organoaluminum oxy-compound (b-2) and the optionally used organoaluminum compound (b-1) are supported in an amount of usually $10^{-5}$ to $10^{-1}$ mol, and preferably $2\times10^{-5}$ to $5\times10^{-2}$ mol per gram of the solid carrier (A) in terms of aluminum atom. When the compound (c-1) is used as the component (C), the compound (c-1) is supported in an amount of usually $10^{-8}$ to $2\times10^{-1}$ mol, and preferably $2\times10^{-8}$ to $10^{-2}$ mol. When the compound (c-2) is used as the component (C), the compound (c-2) is supported in an amount of usually $10^{-8}$ to $3\times10^{-1}$ mol, and preferably $2\times10^{-8}$ to $1.5\times10^{-2}$ mol. When the compound (c-3) is used as the component (C), the compound (c-3) is supported in an amount of usually $2\times10^{-8}$ to $10^{-1}$ mol, and preferably $2\times10^{-8}$ to $2\times10^{-7}$ mol. The transition metal compound (D) is supported in an amount of usually 0.005 to 0.5 mmol, and preferably 0.01 to 0.2 mmol in terms of transition metal atom.

<(E) Organic Compound>

In the present invention, the olefin oligomerization catalyst (III) can optionally further include (E) an organic compound below.

In the present invention, the organic compound (E) is optionally used in order to improve performance of olefin oligomerization. Examples of such an organic compound (E) include alcohols, phenolic compounds, carboxylic acids, phosphorus compounds, and sulfonates.

Examples of the alcohols and the phenolic compounds include compounds represented by $R^{22}$—OH (herein, $R^{22}$ represents a hydrocarbon group having 1 to 50 carbon atoms or a halogenated hydrocarbon group having 1 to 50 carbon atoms). As the above-mentioned alcohols, preferred are compounds in which $R^{22}$ is a halogenated hydrocarbon group. As the above-mentioned phenolic compounds, preferred are compounds in which the α- and α'-positions of a hydroxyl group are substituted by hydrocarbon groups having 1 to 20 carbon atoms.

Examples of the carboxylic acids include compounds represented by $R^{23}$—COOH (herein, $R^{23}$ represents a hydrocarbon group having 1 to 50 carbon atoms or a halogenated hydrocarbon group having 1 to 50 carbon atoms, and preferably a halogenated hydrocarbon group having 1 to 50).

Examples of the phosphorus compounds include phosphoric acids having a P—O—H bond, phosphates and phosphine oxide compounds having a P—OR bond or a P═O bond.

Examples of the sulfonates include salts represented by general formula (vii) below:

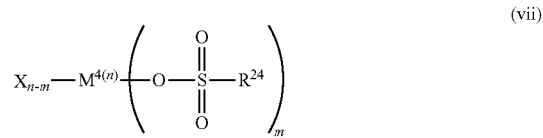

(vii)

In the formula (vii), $M^4$ represents an atom selected from Group I to Group XIV of the periodic table. $R^{24}$ represents hydrogen, a hydrocarbon group having 1 to 20 carbon atoms, or a halogenated hydrocarbon group having 1 to 20 carbon atoms. X represents a hydrogen atom, a halogen atom, a hydrocarbon group having 1 to 20 carbon atoms, or a halogenated hydrocarbon group having 1 to 20 carbon atoms. m represents an integer of 1 to 7, and n represents a valence of M, in which $1\leq n\leq 7$.

A method for using the organic compound (E) is arbitrarily selected, and examples of the method will be given below:

(1) A method in which (B) the organoaluminum oxy-compound (b-2) and the optionally used organoaluminum compound (b-1), and the organic compound (E) are supported on the solid carrier (A) in an arbitrary order;

(2) A method in which the solid catalyst component (I), at least one compound (C) selected from the organometallic compound (c-1), the organoaluminum oxy-compound (c-2), and a compound (c-3) that reacts with the transition metal compound (D) to form a pair of ions, and the organic compound (E) are contacted with each other in an arbitrary order; and (3) A method in which the preliminary contact solid catalyst component (II), the transition metal compound (D), and the organic compound (E) are contacted with each other in an arbitrary order.

When the organoaluminum oxy-compound (b-2) is used as the component (B), the organic compound (E) is used in such an amount that a mole ratio [(E)/(b-2)] of the organic compound (E) to aluminum atoms in the compound (b-2) is usually 0.001 to 2, and preferably 0.005 to 1. In addition, when the organoaluminum compound (b-1) is further used in combination as the component (B), the compound (b-1) is used in such an amount that a mole ratio [ (E)/(b-1)] is usually 0.01 to 10, and preferably 0.1 to 5.

The olefin oligomerization catalyst (III) of the present invention can be suitably used for oligomerization of an olefin. Examples of the olefin to be oligomerized include α-olefins such as ethylene, propylene, 1-butene, 1-pentene, 1-hexene, 4-methyl-1-pentene, 1-octene, and 1-decene; internal olefins such as 2-butene, cyclopentane, cyclohexene, and norbornane; and vinyl compounds having other olefin bonds, such as vinylcyclohexene and stylene. Among these olefins, ethylene is particularly preferable.

In oligomerization of the above-mentioned olefins, one kind thereof alone may be oligomerized, or two or more of the olefins may be combined to perform co-oligomerization.

Hereinafter, a description will be given of a method for producing an olefin oligomer in which an oligomerization reaction of an olefin is performed in the presence of the olefin oligomerization catalyst (III).

[Method for Producing Olefin Oligomer]

A method for producing an olefin oligomer according to the present invention is performed by an oligomerization reaction of an olefin, and preferably by a trimerization reaction or a tetramerization reaction of an olefin in the presence of the above-described olefin oligomerization catalyst (III). Preferred is an ethylene oligomerization reaction using ethylene as an olefin, and particularly preferred are a method for producing 1-hexene by ethylene trimerization and a method for producing 1-octene by ethylene tetramerization.

In the present invention, oligomerization reaction can be performed in both a liquid-phase reaction, such as dissolution reaction or suspension reaction, and a gas-phase reaction.

The liquid-phase reaction uses, as a solvent, an organic compound inactive to the above-described olefin oligomerization catalyst (III) and an olefin component. Examples of the organic compound to be used as the solvent include aliphatic hydrocarbons such as propane, butane, isobutene, pentane, isopentane, hexane, heptane, octane, decane, dodecane, and kerosene; alicyclic hydrocarbons such as cyclopentane, cyclohexane, and methylcyclopentane; aromatic hydrocarbons such as benzene, toluene, xylene, trimethylbenzene, and tetralin; halogenated hydrocarbons such as ethylene chloride, chlorobenzene, and dichloromethane, and mixtures thereof. Among these organic compounds, pentane, n-hexane, and n-heptane are particularly preferable.

In an olefin oligomerization reaction using such an olefin oligomerization catalyst, an organoaluminum compound (F) can be optionally used. Examples of compounds belonging to the organoaluminum compound (F) include the same ones as those of the organoaluminum compound (b-1) described above. Among them, trialkylaluminum is preferable, and triisobutylaluminum is particularly preferable.

In an olefin oligomerization reaction using such an olefin oligomerization catalyst, an organic compound (G) can be optionally used. Examples of compounds belonging to the organic compound (G) include the same ones as those of the organic compound (E) described above.

In performing an oligomerization reaction, a method for adding the above-described olefin oligomerization catalyst (III) (hereinafter referred to simply as "component (III)") in a reactor, a using method for each component, an addition method therefor, and an addition order therefor are arbitrarily selected. Examples of the methods will be given below:

(1) A method in which the component (III) alone is added into a reactor;

(2) A method in which the component (III) and the organoaluminum compound (F) are added into a reactor in an arbitrary order;

(3) A method in which a catalyst prepared by contacting the component (III) with the organoaluminum compound (F) in advance is added into a reactor;

(4) A method in which the component (III) and the organic compound (G) are added into a reactor in an arbitrary order;

(5) A method in which a catalyst prepared by contacting the component (III) with the organic compound (G) in advance is added into a reactor;

(6) A method in which the component (III), the organoaluminum compound (F), and the organic compound (G) are added into a reactor in an arbitrary order;

(7) A method in which a catalyst prepared by contacting the component (III), the organoaluminum compound (F), and the organic compound (G) with each other in advance in an arbitrary order is added into a reactor;

(8) A method in which a catalyst component prepared by contacting the component (III) with the organoaluminum compound (F) in advance and the organic compound (G) are added into a reactor in an arbitrary order;

(9) A method in which a catalyst component prepared by contacting the component (III) with the organic compound (G) in advance and the organoaluminum compound (F) are added into a reactor in an arbitrary order; and

(10) A method in which a catalyst component prepared by contacting the organoaluminum compound (F) with the organic compound (G) in advance and the component (III) are added into a reactor in an arbitrary order.

When an olefin oligomer is produced by oligomerizing an olefin using the olefin oligomerization catalyst as described above, and preferably when 1-hexene is produced by ethylene trimerization or 1-octene is produced by ethylene tetramerization, the transition metal compound (D) is used in such an amount of usually $10^{-12}$ to $10^{-2}$ mol, and preferably $10^{-10}$ to $10^{-3}$ mol per liter of reaction volume. In the present invention, even when the transition metal compound (D) is used in a relatively low concentration, the olefin oligomer can be obtained with high oligomerization activity.

The organoaluminum compound (F) is used with respect to the transition metal compound (D) in such an amount that a mole ratio (Al(F)/M) of aluminum atoms (Al(F)) in the organoaluminum compound (F) to the transition metal atoms (M) in the transition metal compound (D) is usually 0.01 to 1000, and preferably 0.05 to 500.

When the organoaluminum oxy-compound (b-2) is used as the component (B), the organic compound (G) is used in such an amount that a mole ratio [(G)/(b-2)] of the organic compound (G) to aluminum atoms in the compound (b-2) is usually 0.001 to 2, and preferably 0.005 to 1. In addition, when the organoaluminum compound (b-1) is further used in combination as the component (B), the compound (b-1) is used in such an amount that a mole ratio [(G)/(b-1)] is usually 0.01 to 10, and preferably 0.1 to 5.

The reaction temperature for olefin oligomerization using such an olefin oligomerization catalyst is in a range of usually −50 to 200° C., and preferably 0 to 170° C. The reaction pressure condition is usually atmospheric pressure to 10 MPa, and preferably atmospheric pressure to 5 MPa. In addition, the olefin oligomerization reaction may be performed by any of a batchwise method, a semi-continuous method, and a continuous method.

The olefin oligomerization reaction using such an olefin oligomerization catalyst may be performed by adding an antistatic agent. Preferred examples of the antistatic agent include polypropylene glycol, polypropylene glycol distearate, ethylenediamine-PEG-PPG-block copolymer, stearyl diethanolamine, lauryldiethanolamine, alkyldiethanolamide, and polyoxyalkylene (for example, polyethylene glycol-polypropylene glycol-polyethylene glycol block copolymer (PEG-PPG-PEG)), and particularly preferred is polyoxyalkylene (PEG-PPG-PEG). These antistatic agents are used in such an amount that a ratio (g/mol) of a mass (g) thereof to 1 mole of the transition metal atoms (M) in the transition metal compound (D) is usually 100 to 10000, and preferably 100 to 1000.

In addition, the olefin oligomerization reaction may be performed by adding hydrogen. The pressure condition of hydrogen in the reaction is usually 0.01 to 5 MPa, and preferably 0.01 to 1 MPa.

EXAMPLES

Hereinafter, the present invention will be described in detail based on Examples, but is not limited thereto.

Yield of a reaction product and selectivity of 1-hexene (1-octene, and decenes) were analyzed using gas chromatography (Shimadzu GC-14A, J&W Scientific DB-5 column).

[Catalytic Activity]

Catalytic activity was obtained by dividing a mass of a reaction product obtained per unit time by an amount (mmol) of transition metal atoms included in a transition metal catalyst component used for oligomerization.

[Selectivity of 1-Hexene 1-octene (Decenes)]

Selectivity of 1-hexene (1-octene, and decenes) was obtained according to the following formula:

$$S\ (\%)=Wp/Wr \times 100$$

S (%): Selectivity (weight fraction) of 1-hexene
Wr (weight): Total weight of products having 4 or more carbon atoms generated by reaction
Wp (weight): Weight of 1-hexene generated by reaction In addition, selectivity of each of 1-octene and decenes was also obtained according to the above method.

[Tap Density]

Tap density (g/cm$^3$) of by-produced polyethylene particles was measured as follows:

About 200 mg of by-produced polyethylene particles were placed in a 1 mL plastic graduated cylinder (minimum scale unit: 0.01 mL) to measure the mass. Then, on a stone table, the cylinder was tapped by hand at a tap rate of about 250 times/minute with a drop height of about 3 mm. Bulk volume was measured every several tens of times of tapping, and tapping was performed until a volume change in continuously measured bulk volumes became 0.01 mL or less, thereby obtaining a final tap volume. The tap density (g/cm$^3$) was obtained by dividing the previously measured mass of the by-produced polyethylene particles by the final tap volume.

[Volatile Matter]

Volatile matter VM (wt %) in the by-produced polyethylene particles was obtained, according to the following formula, by measuring a mass W1 immediately after filtering the by-produced polyethylene particles out from a reaction solution and then performing pressure-reduced drying at 80° C. for 1 hour to again measure a mass W2.

$$VM\ (\%)=(W1-W2)/W1 \times 100$$

[Ethylene Polymer Observation Method]

The by-produced polyethylene particles were observed by a scanning electron microscope (JEOL JSM-6510LV), whereby shapes of the particles were compared with that of a solid catalyst component to determine the presence or absence of hollow particles.

Hereinafter, a description will be given of specific Examples and Comparative Examples of the method for preparing the olefin oligomerization catalyst of the present invention and ethylene oligomerization.

Example 1

Preparation of Solid Catalyst Component (I-1)

An amount of 8.0 kg of silica (trade name: M. S. GEL, produced by AGC Si-Tech Co., Ltd.) having a mean particle size of 50 μm was dispersed in 82.0 L of toluene, and the temperature of the dispersion was increased to 50° C. Into the resulting slurry was added a solution prepared by diluting 3.4 kg of a triisobutylaluminum toluene solution (produced by Tosoh Finechem Corporation; Al concentration: 2.1 wt %) with 3.0 L of toluene, while stirring under a nitrogen atmosphere. Next, a solution prepared by diluting 23.5 L of a toluene solution of polymethylaluminoxane (produced by Tosoh Finechem Corporation; Al concentration: 9.1 wt %) with 23.5 L of toluene was added into the mixture in 40 minutes. During this period of time, the temperature of the reaction mixture was maintained at 50 to 53° C. After finishing the dropping, the reaction mixture was stirred for another 30 minutes while maintaining the temperature, and then, the temperature was increased to 95° C. in 45 minutes. The temperature of the reaction mixture was maintained at 95 to 100° C. for 4 hours, then reduced down to 60° C., and the stirring was stopped. After sedimentation of particles, 73 L of supernatant toluene was extracted through a dip nozzle, 95 L of toluene was added, and then stirring was performed for 30 minutes. Then, again, the stirring was stopped to allow the reaction mixture to stand still, and then, 95 L of supernatant toluene was extracted through the dip nozzle. This washing operation was performed twice at 60° C., and twice at room temperature. After that, 33 L of toluene was added to obtain a toluene slurry of a solid catalyst component (I-1) having a slurry concentration adjusted to 126 g/L.

Preparation of Preliminary Contact Solid Catalyst Component (II-1)

An amount of 30 mL of the toluene slurry of the above solid catalyst component (I-1) was allowed to stand still and 17.1 mL of supernatant toluene was extracted, 10 mL of the slurry was collected while stirring and charged into a sufficiently nitrogen-substituted 50 mL flask. A solution prepared by diluting 0.11 mL of a toluene solution of polymethylaluminoxane (produced by Tosoh Finechem Corporation; Al concentration: 9.0 wt %) with 6.29 mL of toluene was added therein, and the mixture was stirred at room temperature for 3 hours to obtain a toluene slurry of a preliminary contact solid catalyst component (II-1).

Preparation of Olefin Oligomerization Catalyst (III-1)

Into the toluene slurry of the above preliminary contact solid catalyst component (II-1) was added 12.9 mL of a toluene solution (concentration: 2.5 mmol/L) of a titanium compound 9 described in Patent Literature 4 shown below. The mixture was stirred at room temperature for 3 hours, and then the stirring was stopped. After sedimentation of particles, 10 mL of supernatant toluene was extracted. Then, 35 mL of toluene was added and the mixture was stirred for 10 minutes. After stopping the stirring to allow the mixture to stand still, 35 mL of supernatant toluene was extracted through a dip nozzle. Next, 30 mL of toluene was added and the mixture was stirred for 10 minutes. Then, after stopping the stirring to allow the mixture to stand still, 30 mL of supernatant toluene was extracted through the dip nozzle. This washing operation was repeated twice, and then, 10 mL of toluene was added to obtain a toluene slurry of an olefin oligomerization catalyst (III-1) having a slurry concentration adjusted to 87 g/L.

Compound 9

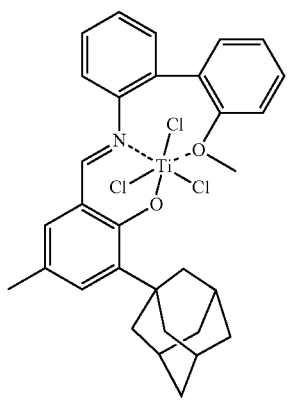

(Oligomerization Reaction)

In a sufficiently nitrogen-substituted autoclave with an internal volume of 500 mL was placed 150 mL of n-heptane to which 0.05 mmol of triisobutylaluminum (1.0 M toluene solution) in terms of aluminum atom had been added, followed by stirring. Next, 1 mL of a toluene solution (concentration: 6 g/L) of ADEKA PLURONIC L-71 (produced by ADEKA Corporation) was added. A toluene slurry prepared by diluting 0.455 mL of the toluene slurry of the above olefin oligomerization catalyst (III-1) with 4 mL of toluene was added into the reactor, followed by pressurization with ethylene (partial pressure: 4.0 MPa-G) to start reaction. While supplying ethylene at the same pressure, the reaction was performed at 45 to 52° C. for 60 minutes and then stopped by adding a small amount of methanol. After finishing the reaction, the reaction solution was washed with 0.1 N hydrochloric acid solution and pure water. Then, Low-boiling components (having 10 or less carbon atoms) were separated from high-boiling components and polyethylene by using a liquid nitrogen trap under reduced pressure. The resulting products were analyzed by gas chromatography. Among the products, 1-hexene had a selectivity of 87%. As the other products, decenes had a selectivity of 12%, and polyethylene had a selectivity of 1.0%. A catalytic activity calculated from a total amount of the products was 74 kg-products/(mmol-Ti·h) (the selectivity of each product calculated to the first decimal place is as follows: 1-hexene selectivity 86.7%; decene selectivity 12.3%; and polyethylene selectivity 1.0%). The polyethylene particles had a volatile matter of 21% and a tap density of 0.50 g/mL.

Figure 2:
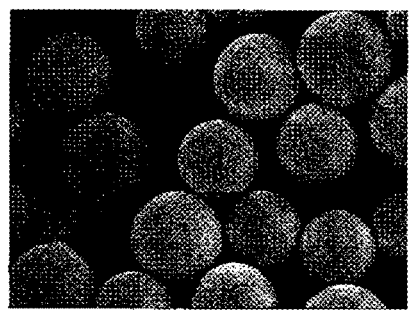
FIG. 2 is an electromicroscopic photograph (200 times) of by-produced polyethylene obtained by reaction in Example 1.

FIG. 1 depicts an electromicroscopic photograph (200 times) of the solid catalyst component (I-1), and FIG. 2 depicts an electromicroscopic photograph (200 times) of the by-produced polyethylene particles. The by-produced polyethylene particles maintain the shape of the solid catalyst component (I-1), thus indicating no occurrence of hollow particles.

Example 2

Preparation of Preliminary Contact Solid Catalyst Component (II-2)

A toluene slurry of a preliminary contact solid catalyst component (II-2) was obtained in the same manner as Example 1, except that, in the preparation of the preliminary contact solid catalyst component (II-1) of Example 1, a solution prepared by diluting 0.21 mL of a toluene solution of polymethylaluminoxane (produced by Tosoh Finechem Corporation; Al concentration: 9.0 wt %) with 6.19 mL of toluene was used instead of the solution prepared by diluting 0.11 mL of the toluene solution of polymethylaluminoxane (produced by Tosoh Finechem Corporation; Al concentration: 9.0 wt %) with 6.29 mL of toluene.

Preparation of Olefin Oligomerization Catalyst (III-2)

A toluene slurry of an olefin oligomerization catalyst (III-2) was obtained in the same manner as Example 1, except that, in the preparation of the olefin oligomerization catalyst (III-1) of Example 1, the toluene slurry of the preliminary contact solid catalyst component (II-2) was used instead of the toluene slurry of the preliminary contact solid catalyst component (II-1).

(Oligomerization Reaction)

An oligomerization reaction was performed in the same manner as Example 1, except that, in the oligomerization reaction of Example 1, the toluene slurry of the olefin oligomerization catalyst (III-2) was used instead of the toluene slurry of the olefin oligomerization catalyst (III-1). After finishing the reaction, the reaction solution was washed with 0.1 N hydrochloric acid solution and pure water. Then, Low-boiling components (having 10 or less carbon atoms) were separated from high-boiling components and polyethylene by using a liquid nitrogen trap under reduced pressure. The resulting products were analyzed by gas chromatography. Among the products, 1-hexene had a selectivity of 86%. As the other products, decenes had a selectivity of 13%, and polyethylene had a selectivity of 1.2%. A catalytic activity calculated from a total amount of the products was 70 kg-products/(mmol-Ti·h) (the selectivity of each product calculated to the first decimal place is as follows: 1-hexene selectivity 86.10; decene selectivity 12.70; and polyethylene selectivity 1.2%). The polyethylene particles had a volatile matter of 20% and a tap density of 0.54 g/mL. No hollow particles were observed.

Example 3

Preparation of Preliminary Contact Solid Catalyst Component (II-3)

A toluene slurry of a preliminary contact solid catalyst component (II-3) was obtained in the same manner as Example 1, except that, in the preparation of the preliminary contact solid catalyst component (II-1) of Example 1, a solution prepared by diluting 0.32 mL of a toluene solution of polymethylaluminoxane (produced by Tosoh Finechem Corporation; Al concentration: 9.0 wt %) with 6.08 mL of toluene was used instead of the solution prepared by diluting 0.11 mL of the toluene solution of polymethylaluminoxane (produced by Tosoh Finechem Corporation; Al concentration: 9.0 wt %) with 6.29 mL of toluene.

Preparation of Olefin Oligomerization Catalyst (III-3)

A toluene slurry of an olefin oligomerization catalyst (III-3) was obtained in the same manner as Example 1, except that, in the preparation of the olefin oligomerization catalyst (III-1) of Example 1, the toluene slurry of the preliminary contact solid catalyst component (II-3) was used instead of the toluene slurry of the preliminary contact solid catalyst component (II-1).
(Oligomerization Reaction)

An oligomerization reaction was performed in the same manner as Example 1, except that, in the oligomerization reaction of Example 1, the toluene slurry of the olefin oligomerization catalyst (III-3) was used instead of the toluene slurry of the olefin oligomerization catalyst (III-1). After finishing the reaction, the reaction solution was washed with 0.1 N hydrochloric acid solution and pure water. Then, Low-boiling components (having 10 or less carbon atoms) were separated from high-boiling components and polyethylene by using a liquid nitrogen trap under reduced pressure. The resulting products were analyzed by gas chromatography. Among the products, 1-hexene had a selectivity of 87%. As the other products, decenes had a selectivity of 13%, and polyethylene had a selectivity of 1.0%. A catalytic activity calculated from a total amount of the products was 69 kg-products/(mmol-Ti·h) (the selectivity of each product calculated to the first decimal place is as follows: 1-hexene selectivity 86.5%; decene selectivity 12.5%; and polyethylene selectivity 1.0%). The polyethylene particles had a volatile matter of 24% and a tap density of 0.51 g/mL. No hollow particles were observed.

Comparative Example 1

Preparation of Preliminary Contact Solid Catalyst Component (II-Comp. 1)

A toluene slurry of a preliminary contact solid catalyst component (II-Comp. 1) was obtained in the same manner as Example 1, except that, in the preparation of the preliminary contact solid catalyst component (II-1) of Example 1, 6.4 mL of toluene was used instead of the solution prepared by diluting 0.11 mL of the toluene solution of polymethylaluminoxane (produced by Tosoh Finechem Corporation; Al concentration: 9.0 wt %) with 6.29 mL of toluene.

Preparation of Olefin Oligomerization Catalyst (III-Comp. 1)

A toluene slurry of an olefin oligomerization catalyst (III-Comp. 1) was obtained in the same manner as Example 1, except that, in the preparation of the olefin oligomerization catalyst (III-1) of Example 1, the toluene slurry of the preliminary contact solid catalyst component (II-Comp. 1) was used instead of the toluene slurry of the preliminary contact solid catalyst component (II-1).
(Oligomerization Reaction)

An oligomerization reaction was performed in the same manner as Example 1, except that, in the oligomerization reaction of Example 1, the toluene slurry of the olefin oligomerization catalyst (III-Comp. 1) was used instead of the toluene slurry of the olefin oligomerization catalyst (III-1). After finishing the reaction, the reaction solution was washed with 0.1 N hydrochloric acid solution and pure water. Then, Low-boiling components (having 10 or less carbon atoms) were separated from high-boiling components and polyethylene by using a liquid nitrogen trap under reduced pressure. The resulting products were analyzed by gas chromatography. Among the products, 1-hexene had a selectivity of 87%. As the other products, decenes had a selectivity of 12%, and polyethylene had a selectivity of 1.1%. A catalytic activity calculated from a total amount of the products was 53 kg-products/(mmol-Ti·h) (the selectivity of each product calculated to the first decimal place is as follows: 1-hexene selectivity 86.7%; decene selectivity 12.2%; and polyethylene selectivity 1.1%). The polyethylene particles had a volatile matter of 40% and a tap density of 0.36 g/mL.

Figure 3:
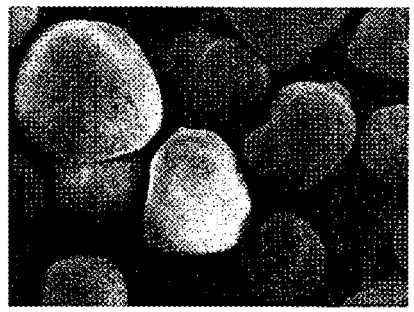
FIG. 3 is an electromicroscopic photograph (200 times) of by-produced polyethylene obtained by reaction in Comparative Example 1.

FIG. 3 depicts an electromicroscopic photograph (200 times) of the by-produced polyethylene particles. The by-produced polyethylene particles have shapes significantly different from the shape of the solid catalyst component (I-1) depicted in FIG. 1, thus indicating occurrence of hollow particles.

Example 4

Preparation of Solid Catalyst Component (I-2)

An amount of 7.4 kg of silica (trade name: M. S. GEL, produced by AGC Si-Tech Co., Ltd.) having a mean particle size of 30 μm was dispersed in 86.0 L of toluene, and the temperature of the dispersion was increased to 50° C. Into the resulting slurry was added a solution prepared by diluting 2.4 kg of a triisobutylaluminum toluene solution (produced by Tosoh Finechem Corporation; Al concentration: 2.1 wt %) with 3.7 L of toluene, while stirring under a nitrogen atmosphere. Next, a solution prepared by diluting 22.0 L of a toluene solution of polymethylaluminoxane (produced by Tosoh Finechem Corporation; Al concentration: 9.0 wt %) with a 22.0 L of toluene was added in 40 minutes. During this period of time, the temperature of the reaction mixture was maintained at 50 to 53° C. After finishing the dropping, the reaction mixture was stirred for another 30 minutes while maintaining the temperature, and then the temperature was increased to 95° C. in 45 minutes. The temperature of the reaction mixture was maintained at 95 to 100° C. for 4 hours, then reduced down to 60° C., and the stirring was stopped. After sedimentation of particles, 77 L of supernatant toluene was extracted through a dip nozzle. After adding 90 L of toluene and stirring for 30 minutes, stirring was again stopped to allow the mixture to stand still, and then, 90 L of supernatant toluene was extracted through the dip nozzle. After this washing operation was performed twice at 60° C. and twice at room temperature, 30 L of toluene was added to obtain a toluene slurry of a solid catalyst component (I-2) having a slurry concentration adjusted to 125 g/L.

Preparation of Preliminary Contact Solid Catalyst Component (II-4)

After 30 mL of the toluene slurry of the above solid catalyst component (I-2) was allowed to stand still and 17.8 mL of supernatant toluene was extracted, 10 mL of the slurry was collected while stirring and charged into a sufficiently nitrogen-substituted 50 mL flask. A solution prepared by diluting 0.11 mL of a toluene solution of polymethylaluminoxane (produced by Tosoh Finechem Corporation; Al concentration: 8.9 wt %) with 6.36 mL of toluene was added therein, and the mixture was stirred at room temperature for 3 hours to obtain a toluene slurry of a preliminary contact solid catalyst component (II-4).

Preparation of Olefin Oligomerization Catalyst (III-4)

Into the toluene slurry of the above preliminary contact solid catalyst component (II-4) was added 12.9 mL of a toluene solution (concentration: 2.5 mmol/L) of the above titanium compound 9 described in Patent Literature 4. The mixture was stirred at room temperature for 3 hours, and then the stirring was stopped. After sedimentation of particles, 10 mL of supernatant toluene was extracted. Next, 35 mL of toluene was added and the mixture was stirred for 10 minutes. After stopping the stirring to allow the mixture to stand still, 35 mL of supernatant toluene was extracted through a dip nozzle. Then, 30 mL of toluene was added, and the mixture was stirred for 10 minutes. After stopping the stirring to allow the mixture to stand still, 30 mL of supernatant toluene was extracted through the dip nozzle. This washing operation was repeated twice, and then, 10 mL of toluene was added to obtain a toluene slurry of an olefin oligomerization catalyst (III-4) having a slurry concentration adjusted to 74 g/L.

(Oligomerization Reaction)

In a sufficiently nitrogen-substituted autoclave with an internal volume of 500 mL was placed 150 mL of n-heptane to which 0.05 mmol of triisobutylaluminum (1.0 M toluene solution) in terms of aluminum atom had been added, followed by stirring. Next, 1 mL of a toluene solution (concentration: 6 g/L) of ADEKA PLURONIC L-71 (produced by ADEKA Corporation) was added. A toluene slurry prepared by diluting 0.455 mL of the toluene slurry of the above olefin oligomerization catalyst (III-4) with 4 mL of toluene was added into the reactor, followed by pressurization with ethylene (partial pressure: 4.5 MPa-G) to start reaction. While supplying ethylene at the same pressure, the reaction was performed at 45 to 52° C. for 60 minutes, and then stopped by adding a small amount of methanol. After finishing the reaction, the reaction solution was washed with 0.1 N hydrochloric acid solution and pure water, and the resulting products were analyzed by gas chromatography. Among the products, 1-hexene had a selectivity of 86%. As the other products, decenes had a selectivity of 12%, and polyethylene had a selectivity of 0.9%. A catalytic activity calculated from a total amount of the products was 130 kg-products/(mmol-Ti·h) (the selectivity of each product calculated to the first decimal place is as follows: 1-hexene selectivity 86.3%; decene selectivity 12.8%; and polyethylene selectivity 0.9%). The polyethylene particles had a volatile matter of 15% and a tap density of 0.55 g/mL. No hollow particles were observed.

Example 5

Preparation of Preliminary Contact Solid Catalyst Component (II-5)

A toluene slurry of a preliminary contact solid catalyst component (II-5) was obtained in the same manner as Example 4, except that, in the preparation of the preliminary contact solid catalyst component (II-4) of Example 4, a solution prepared by diluting 0.05 mL of a toluene solution of polymethylaluminoxane (produced by Tosoh Finechem Corporation; Al concentration: 8.9 wt %) with 6.42 mL of toluene was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-5)

A toluene slurry of an olefin oligomerization catalyst (III-5) was obtained in the same manner as Example 4, except that, in the preparation of the olefin oligomerization catalyst (III-4) of Example 4, the toluene slurry of the preliminary contact solid catalyst component (II-5) was used instead of the toluene slurry of the preliminary contact solid catalyst component (II-4).

(Oligomerization Reaction)

An oligomerization reaction was performed in the same manner as Example 4, except that, in the oligomerization reaction of Example 4, the toluene slurry of the olefin oligomerization catalyst (III-5) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 86%. As the other products, decenes had a selectivity of 13%, and polyethylene had a selectivity of 0.8%. A catalytic activity calculated from a total amount of the products was 121 kg-products/(mmol-Ti·h) (the selectivity of each product calculated to the first decimal place is as follows: 1-hexene selectivity 86.3%; decene selectivity 12.9%; and polyethylene selectivity 0.8%). The polyethylene particles had a volatile matter of 24% and a tap density of 0.56 g/mL. No hollow particles were observed.

Example 6

Preparation of Preliminary Contact Solid Catalyst Component (II-6)

A toluene slurry of a preliminary contact solid catalyst component (II-6) was obtained in the same manner as Example 4, except that, in the preparation of the preliminary contact solid catalyst component (II-4) of Example 4, a solution prepared by diluting 0.22 mL of a toluene solution of polymethylaluminoxane (produced by Tosoh Finechem Corporation; Al concentration: 8.9 wt %) with 6.26 mL of toluene was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-6)

A toluene slurry of an olefin oligomerization catalyst (III-6) was obtained in the same manner as Example 4, except that, in the preparation of the olefin oligomerization catalyst (III-4) of Example 4, the toluene slurry of the preliminary contact solid catalyst component (II-6) was used instead of the toluene slurry of the preliminary contact solid catalyst component (II-4).

(Oligomerization Reaction)

An oligomerization reaction was performed in the same manner as Example 4, except that, in the oligomerization reaction of Example 4, the toluene slurry of the olefin oligomerization catalyst (III-6) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 87%. As the other products, decenes had a selectivity of 13%, and polyethylene had a selectivity of 0.9%. A catalytic activity calculated from a total amount of the products was 132 kg-products/(mmol·Ti·h) (the selectivity of each product calculated to the first decimal place is as follows: 1-hexene selectivity 86.6%; decene selectivity 12.5%; and polyethylene selectivity 0.9%). The polyethylene particles had a volatile matter of 27% and a tap density of 0.57 g/mL. No hollow particles were observed.

Comparative Example 2

Preparation of Preliminary Contact Solid Catalyst Component (II-Comp. 2)

A toluene slurry of a preliminary contact solid catalyst component (II-Comp. 2) was obtained in the same manner as Example 4, except that, in the preparation of the preliminary contact solid catalyst component (II-4) of Example 4, 6.47 mL of toluene was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-Comp. 2)

A toluene slurry of an olefin oligomerization catalyst (III-Comp. 2) was obtained in the same manner as Example 4, except that, in the preparation of the olefin oligomerization catalyst (III-4) of Example 4, the toluene slurry of the preliminary contact solid catalyst component (II-Comp. 2) was used instead of the toluene slurry of the preliminary contact solid catalyst component (II-4).

(Oligomerization Reaction)

An oligomerization reaction was performed in the same manner as Example 4, except that, in the oligomerization reaction of Example 4, the toluene slurry of the olefin oligomerization catalyst (III-Comp. 2) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 87%. As the other products, decenes had a selectivity of 12%, and polyethylene had a selectivity of 1.0%. A catalytic activity calculated from a total amount of the products was 120 kg-products/(mmol·Ti·h) (the selectivity of each product calculated to the first decimal place is as follows: 1-hexene selectivity 86.8%; decene selectivity 12.2%; and polyethylene selectivity 1.0%). The polyethylene particles had a volatile matter of 42% and a tap density of 0.38 g/mL. Hollow particles were observed.

Example 7

Preparation of Preliminary Contact Solid Catalyst Component (II-7)

A toluene slurry of a preliminary contact solid catalyst component (II-7) was obtained in the same manner as Example 4, except that, in the preparation of the preliminary contact solid catalyst component (II-4) of Example 4, a solution prepared by diluting 0.16 mL of a hexane solution of methylaluminoxane (MMAO-3A, produced by Tosoh Finechem Corporation; Al concentration: 2.13 mol/L) with 6.31 mL of toluene was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-7)

A toluene slurry of an olefin oligomerization catalyst (III-7) was obtained in the same manner as Example 4, except that, in the preparation of the olefin oligomerization catalyst (III-4) of Example 4, the toluene slurry of the preliminary contact solid catalyst component (II-7) was used instead of the toluene slurry of the preliminary contact solid catalyst component (II-4).

(Oligomerization Reaction)

An oligomerization reaction was performed in the same manner as Example 4, except that, in the oligomerization reaction of Example 4, the toluene slurry of the olefin oligomerization catalyst (III-7) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 86%. As the other products, decenes had a selectivity of 13%, and polyethylene had a selectivity of 0.8%. A catalytic activity calculated from a total amount of the products was 132 kg-products/(mmol·Ti·h) (the selectivity of each product calculated to the first decimal place is as follows: 1-hexene selectivity 86.4%; decene selectivity 12.8%; and polyethylene selectivity 0.8%). The polyethylene particles had a volatile matter of 32% and a tap density of 0.53 g/mL. No hollow particles were observed.

Example 8

Preparation of Preliminary Contact Solid Catalyst Component (II-8)

A toluene slurry of a preliminary contact solid catalyst component (II-8) was obtained in the same manner as Example 4, except that, in the preparation of the preliminary contact solid catalyst component (II-4) of Example 4, a solution prepared by diluting 0.11 mL of a toluene solution of methylaluminoxane (produced by Albemarle, Inc.; Al concentration: 3.0 mol/L) with 6.36 mL of toluene was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-8)

A toluene slurry of an olefin oligomerization catalyst (III-8) was obtained in the same manner as Example 4, except that, in the preparation of the olefin oligomerization catalyst (III-4) of Example 4, the toluene slurry of the preliminary contact solid catalyst component (II-8) was used instead of the toluene slurry of the preliminary contact solid catalyst component (II-4).

(Oligomerization Reaction)

An oligomerization reaction was performed in the same manner as Example 4, except that, in the oligomerization reaction of Example 4, the toluene slurry of the olefin oligomerization catalyst (III-8) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 87%. As the other products, decenes had a selectivity of 13%, and polyethylene had a selectivity of 0.8%. A catalytic activity calculated from a total amount of the products was 128 kg-products/(mmol-Ti·h) (the selectivity of each product calculated to the first decimal place is as follows: 1-hexene selectivity 86.7%; decene selectivity 12.5%; and polyethylene selectivity 0.8%). The polyethylene particles had a volatile matter of 27% and a tap density of 0.60 g/mL. No hollow particles were observed.

Example 9

Preparation of Preliminary Contact Solid Catalyst Component (II-9)

A toluene slurry of a preliminary contact solid catalyst component (II-9) was obtained in the same manner as Example 4, except that, in the preparation of the preliminary contact solid catalyst component (II-4) of Example 4, 6.47 mL of a solution prepared by diluting a hexane solution of trimethylaluminum (produced by Kanto Chemical Co., Inc.; Al concentration: 1.4 mol/L) with toluene to 0.05 mol/L was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-9)

A toluene slurry of an olefin oligomerization catalyst (III-9) was obtained in the same manner as Example 4, except that, in the preparation of the olefin oligomerization catalyst (III-4) of Example 4, the toluene slurry of the preliminary contact solid catalyst component (II-9) was used instead of the toluene slurry of the preliminary contact solid catalyst component (II-4).
(Oligomerization Reaction)

An oligomerization reaction was performed in the same manner as Example 4, except that, in the oligomerization reaction of Example 4, the toluene slurry of the olefin oligomerization catalyst (III-9) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 87%. As the other products, decenes had a selectivity of 12%, and polyethylene had a selectivity of 0.7%. A catalytic activity calculated from a total amount of the products was 136 kg-products/(mmol-Ti·h) (the selectivity of each product calculated to the first decimal place is as follows: 1-hexene selectivity 87.0%; decene selectivity 12.3%; and polyethylene selectivity 0.7%). The polyethylene particles had a volatile matter of 24% and a tap density of 0.59 g/mL. No hollow particles were observed.

Example 10

Preparation of Preliminary Contact Solid Catalyst Component (II-10)

A toluene slurry of a preliminary contact solid catalyst component (II-10) was obtained in the same manner as Example 4, except that, in the preparation of the preliminary contact solid catalyst component (II-4) of Example 4, 6.47 mL of a solution prepared by diluting a hexane solution of trimethylaluminum (produced by Kanto Chemical Co., Inc.; Al concentration: 1.4 mol/L) with toluene to 0.015 mol/L was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-10)

A toluene slurry of an olefin oligomerization catalyst (III-10) was obtained in the same manner as Example 4, except that, in the preparation of the olefin oligomerization catalyst (III-4) of Example 4, the toluene slurry of the preliminary contact solid catalyst component (II-10) was used instead of the toluene slurry of the preliminary contact solid catalyst component (II-4).
(Oligomerization Reaction)

An oligomerization reaction was performed in the same manner as Example 4, except that, in the oligomerization reaction of Example 4, the toluene slurry of the olefin oligomerization catalyst (III-10) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 88%. As the other products, decenes had a selectivity of 12%, and polyethylene had a selectivity of 0.6%. A catalytic activity calculated from a total amount of the products was 168 kg-products/(mmol-Ti·h) (the selectivity of each product calculated to the first decimal place is as follows: 1-hexene selectivity 87.6%; decene selectivity 11.8%; and polyethylene selectivity 0.6%). The polyethylene particles had a volatile matter of 33% and a tap density of 0.58 g/mL. No hollow particles were observed.

Example 11

Preparation of Preliminary Contact Solid Catalyst Component (II-11)

A toluene slurry of a preliminary contact solid catalyst component (II-11) was obtained in the same manner as Example 4, except that, in the preparation of the preliminary contact solid catalyst component (II-4) of Example 4, 6.47 mL of a solution prepared by diluting a hexane solution of dimethylaluminum chloride (produced by Kanto Chemical Co., Inc.; Al concentration: 1.0 mol/L) with toluene to 0.05 mol/L was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-11)

A toluene slurry of an olefin oligomerization catalyst (III-11) was obtained in the same manner as Example 4, except that, in the preparation of the olefin oligomerization catalyst (III-4) of Example 4, the toluene slurry of the preliminary contact solid catalyst component (II-11) was used instead of the toluene slurry of the preliminary contact solid catalyst component (II-4).
(Oligomerization Reaction)

An oligomerization reaction was performed in the same manner as Example 4, except that, in the oligomerization reaction of Example 4, the toluene slurry of the olefin oligomerization catalyst (III-11) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 87%. As the other products, decenes had a selectivity of 12%, and polyethylene had a selectivity of 1.2%. A catalytic activity calculated from a total amount of the products was 103 kg-products/(mmol·Ti·h) (the selectivity of each product calculated to the first decimal place is as follows: 1-hexene selectivity 86.5%; decene selectivity 12.3%; and polyethylene selectivity 1.2%). The polyethylene particles had a volatile matter of 34% and a tap density of 0.55 g/mL. No hollow particles were observed.

Example 12

Preparation of Preliminary Contact Solid Catalyst Component (II-12)

A toluene slurry of a preliminary contact solid catalyst component (II-12) was obtained in the same manner as Example 4, except that, in the preparation of the preliminary contact solid catalyst component (II-4) of Example 4, 6.47 mL of a solution prepared by diluting a hexane solution of dimethylaluminum chloride (produced by Kanto Chemical Co., Inc.; Al concentration: 1.0 mol/L) with toluene to 0.015 mol/L was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-12)

A toluene slurry of an olefin oligomerization catalyst (III-12) was obtained in the same manner as Example 4, except that, in the preparation of the olefin oligomerization catalyst (III-4) of Example 4, the toluene slurry of the preliminary contact solid catalyst component (II-12) was used instead of the toluene slurry of the preliminary contact solid catalyst component (II-4).
(Oligomerization Reaction)

An oligomerization reaction was performed in the same manner as Example 4, except that, in the oligomerization reaction of Example 4, the toluene slurry of the olefin oligomerization catalyst (III-12) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 87%. As the other products, decenes had a selectivity of 12%, and polyethylene had a selectivity of 0.7%. A catalytic activity calculated from a total amount of the products was 149 kg-products/(mmol·Ti·h) (the selectivity of each product calculated to the first decimal place is as follows: 1-hexene selectivity 87.0%; decene selectivity 12.3%; and polyethylene selectivity 0.7%). The polyethylene particles had a volatile matter of 27% and a tap density of 0.57 g/mL. No hollow particles were observed.

Example 13

Preparation of Preliminary Contact Solid Catalyst Component (II-13)

A toluene slurry of a preliminary contact solid catalyst component (II-13) was obtained in the same manner as Example 4, except that, in the preparation of the preliminary contact solid catalyst component (II-4) of Example 4, 6.47 mL of a solution prepared by diluting a hexane solution of dimethylzinc (produced by Kanto Chemical Co., Inc.; Zn concentration: 1.0 mol/L) with toluene to 0.05 mol/L was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-13)

A toluene slurry of an olefin oligomerization catalyst (III-13) was obtained in the same manner as Example 4, except that, in the preparation of the olefin oligomerization catalyst (III-4) of Example 4, the toluene slurry of the preliminary contact solid catalyst component (II-13) was used instead of the toluene slurry of the preliminary contact solid catalyst component (II-4).
(Oligomerization Reaction)

An oligomerization reaction was performed in the same manner as Example 4, except that, in the oligomerization reaction of Example 4, the toluene slurry of the olefin oligomerization catalyst (III-13) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 88%. As the other products, decenes had a selectivity of 12%, and polyethylene had a selectivity of 0.7%. A catalytic activity calculated from a total amount of the products was 140 kg-products/(mmol·Ti·h) (the selectivity of each product calculated to the first decimal place is as follows: 1-hexene selectivity 87.5%; decene selectivity 11.8%; and polyethylene selectivity 0.7%). The polyethylene particles had a volatile matter of 34% and a tap density of 0.52 g/mL. No hollow particles were observed.

Example 14

Preparation of Preliminary Contact Solid Catalyst Component (II-14)

A toluene slurry of a preliminary contact solid catalyst component (II-14) was obtained in the same manner as Example 4, except that, in the preparation of the preliminary contact solid catalyst component (II-4) of Example 4, 6.47 mL of a solution prepared by diluting a hexane solution of dimethylzinc (produced by Kanto Chemical Co., Inc.; Zn concentration: 1.0 mol/L) with toluene to 0.015 mol/L was used instead of the solution prepared by diluting 0.11 mL of the toluene solution of polymethylaluminoxane (produced by Tosoh Finechem Corporation; Al concentration: 8.9 wt %) with 6.36 mL of toluene.

Preparation of Olefin Oligomerization Catalyst (III-14)

A toluene slurry of an olefin oligomerization catalyst (III-14) was obtained in the same manner as Example 4, except that, in the preparation of the olefin oligomerization catalyst (III-4) of Example 4, the toluene slurry of the preliminary contact solid catalyst component (II-14) was used instead of the toluene slurry of the preliminary contact solid catalyst component (II-4).
(Oligomerization Reaction)
An oligomerization reaction was performed in the same manner as Example 4, except that, in the oligomerization reaction of Example 4, the toluene slurry of the olefin oligomerization catalyst (III-14) was used instead of the toluene slurry of the olefin oligomerization catalyst (III-4). After finishing the reaction, the reaction solution was washed with 0.1 N hydrochloric acid solution and pure water, and the resulting products were analyzed by gas chromatography. Among the products, 1-hexene had a selectivity of 88%. As the other products, decenes had a selectivity of 12%, and polyethylene had a selectivity of 0.6%. A catalytic activity calculated from a total amount of the products was 149 kg-products/(mmol-Ti·h) (the selectivity of each product calculated to the first decimal place is as follows: 1-hexene selectivity 87.6%; decene selectivity 11.8%; and polyethylene selectivity 0.6%). The polyethylene particles had a volatile matter of 29% and a tap density of 0.56 g/mL. No hollow particles were observed.

Example 15

Preparation of Preliminary Contact Solid Catalyst Component (II-15)

In a glove box, 3.05 mL of the toluene slurry of the solid catalyst component (I-2) was charged into a 20 mL flask, and a solution prepared by diluting 0.045 mL of a toluene solution of polymethylaluminoxane (produced by Tosoh Finechem Corporation; Al concentration: 8.9 wt %) with 2.66 mL of toluene was added while stirring. Then, the mixture was stirred at room temperature for 3 hours to obtain a toluene slurry of a preliminary contact solid catalyst component (II-15). —Preparation of Olefin Oligomerization Catalyst (III-15)
An amount of 6 mL (0.06 mmol) of a toluene solution (0.01 mol/L) of (phenyl)$_2$PN(isopropyl)P(phenyl)$_2$ ligand synthesized according to a method described in JP-T-2006-517528 was added to 6 mL (0.03 mmol) of a toluene solution (Cr concentration: 0.005 mol/L) of Cr(acac)$_3$ under a nitrogen atmosphere, and the mixture was stirred at room temperature for 5 minutes. Then, 5.45 mL of the resulting mixture solution was collected and added to the slurry of the component (II-15) obtained above, followed by stirring at room temperature for 3 hours to obtain a toluene slurry of an olefin oligomerization catalyst (III-15).
(Oligomerization Reaction)
In a sufficiently nitrogen-substituted autoclave with an internal volume of 500 mL was placed 150 mL of n-heptane to which 0.1 mmol of trimethylaluminum (2.0 M toluene solution) in terms of aluminum atom had been added, followed by stirring. Next, 4 mL of the toluene slurry of the olefin oligomerization catalyst (III-15) was added into the reactor, followed by pressurization with ethylene (partial pressure: 4.5 MPa-G) to start reaction. While supplying ethylene at the same pressure, the reaction was performed at 45 to 52° C. for 60 minutes, and then stopped by adding a small amount of methanol. After finishing the reaction, the reaction solution was washed with 0.1 N hydrochloric acid solution and pure water, and the resulting products were analyzed by gas chromatography. Among the products, 1-hexene had a selectivity of 15%, 1-octene had a selectivity of 65%, and polyethylene had a selectivity of 10%. A catalytic activity calculated from a total amount of all the products including the other products was 3.5 kg-products/(mmol-Cr·h) (the selectivity of each product calculated to the first decimal place is as follows: 1-hexene selectivity 14.9%; 1-octene selectivity 64.9%; and polyethylene selectivity 10.0%).

Figure 4:
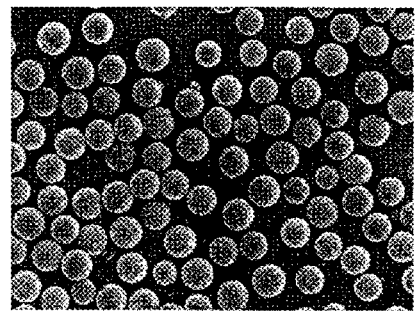
FIG. 4 is an electromicroscopic photograph (200 times) of a solid catalyst component (I-2) used in Example 15.
Figure 5:
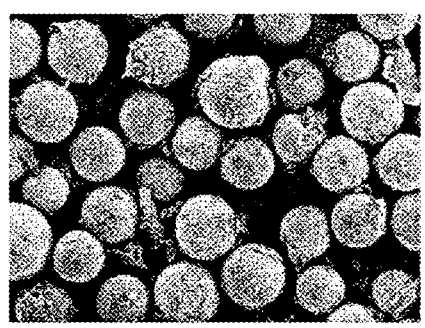
FIG. 5 is an electromicroscopic photograph (200 times) of by-produced polyethylene obtained by reaction in Example 15.

FIG. 4 depicts an electromicroscopic photograph (200 times) of the solid catalyst component (I-2), and FIG. 5 depicts an electromicroscopic photograph (200 times) of the by-produced polyethylene particles. The by-produced polyethylene particles maintain the shape of solid catalyst component (I-2), thus indicating no occurrence of hollow particles.

Comparative Example 3

Preparation of Preliminary Contact Solid Catalyst Component (II-Comp. 3)

A toluene slurry of a preliminary contact solid catalyst component (II-Comp. 3) was obtained in the same manner as Example 15 except that, in the preparation of the preliminary contact solid catalyst component (II-15) of Example 15, 2.7 mL of toluene was used instead of the solution prepared by diluting 0.045 mL of the toluene solution of polymethylaluminoxane (produced by Tosoh Finechem Corporation; Al concentration: 8.9 wt %) with 2.66 mL of toluene.

Preparation of Olefin Oligomerization Catalyst (III-Comp. 3)

A toluene slurry of an olefin oligomerization catalyst (III-Comp. 3) was obtained in the same manner as Example 15, except that, in the preparation of the olefin oligomerization catalyst (III-15) of Example 15, the toluene slurry of the preliminary contact solid catalyst component (II-Comp. 3) was used instead of the toluene slurry of the preliminary contact solid catalyst component (II-15).
(Oligomerization Reaction)
An oligomerization reaction was performed in the same manner as Example 15, except that, in the oligomerization reaction of Example 15, the toluene slurry of the olefin oligomerization catalyst (III-Comp. 3) was used instead of the toluene slurry of the olefin oligomerization catalyst (III-15). After finishing the reaction, the reaction solution was washed with 0.1 N hydrochloric acid solution and pure water, and the resulting products were analyzed by gas chromatography. Among the products, 1-hexene had a selectivity of 14%, 1-octene had a selectivity of 55%, and polyethylene had a selectivity of 21%. A catalytic activity calculated from a total amount of all the products including the other products was 3.5 kg-products/(mmol-Cr·h) (the selectivity of each product calculated to the first decimal place is as follows: 1-hexene selectivity 14.2%; 1-octene selectivity 55.0%; and polyethylene selectivity 21.0%).

Figure 6:
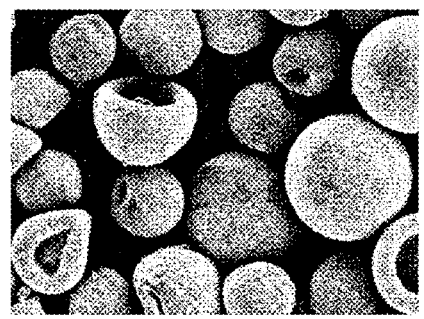
FIG. 6 is an electromicroscopic photograph (200 times) of by-produced polyethylene obtained by reaction in Comparative Example 3.

FIG. 6 depicts an electromicroscopic photograph (200 times) of the by-produced polyethylene particles. The by-produced polyethylene particles have shapes significantly different from the shape of the solid catalyst component (I-2) depicted in FIG. 4, thus indicating occurrence of hollow particles.

The results of the Examples and the Comparative Examples described above have clearly shown that, in the olefin oligomerization reactions using the olefin oligomerization catalysts according to the present invention, the particles of the by-produced polymer component do not become hollow as compared to those using the conventionally known olefin oligomerization catalysts. The reason for this is assumed to be that, as described above, the olefin oligomerization catalyst (III) is obtained in such a manner that the transition metal compound (D) is distributed to the inside of the preliminary contact solid catalyst component (II) due to the formation of a space by the change of the molecular structure of the organoaluminum oxy-compound (b-2) supported on the surface of the solid catalyst component (I) in the preparation of the preliminary contact solid catalyst component (II) according to the invention.

INDUSTRIAL APPLICABILITY

When an olefin oligomerization reaction is performed using the olefin oligomerization catalyst according to the present invention, particles of a polymer component by-produced in the olefin oligomerization reaction do not become hollow. Thus, production process can be simplified, which is highly valuable in industry.

The invention claimed is:

1. An olefin oligomerization catalyst (III) obtained by contacting (D) a transition metal compound having a transition metal atom selected from Group III to Group X of the periodic table with a preliminary contact solid catalyst component (II) obtained by contacting a solid catalyst component (I) formed by supporting (B) an organoaluminum oxy-compound (b-2) on (A) a solid carrier with (C) at least one compound selected from the group consisting of an organometallic compound (c-1), an organoaluminum oxy-compound (c-2), and a compound (c-3) that reacts with the transition metal compound (D) to form a pair of ions, wherein the transition metal compound (D) is represented by general formula (1) below:

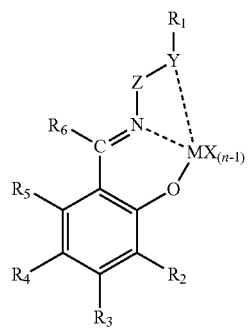

(1)

in the general formula (1), $R^1$ to $R^6$ may be the same as or different from each other and each represent a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group, or a tin-containing group, in which two or more thereof may be linked to each other, and $R^1$ may be linked to Z;

M represents a transition metal atom selected from Group III to Group X of the periodic table;

n represents a valence of M;

X represents a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group, or a tin-containing group, in which atoms or groups represented by X may be the same as or different from each other, and the groups represented by X may be linked to each other to form a ring;

Y represents an oxygen atom, a nitrogen atom, a phosphorus atom, or a sulfur atom;

Z represents a hydrocarbon group or a heterocyclic compound residue that may have a substituent, and the minimum number of bonds linking Y and N is 4 to 6;

in the formula, a bond linking Y and Z may be a double bond or a triple bond, and a bond linking Y and $R^1$ may be a double bond or a triple bond; and in the formula, each dotted line represents a coordination bond.

2. The olefin oligomerization catalyst (III) according to claim 1, further including an organoaluminum compound (b-1) as the component (B).

3. The olefin oligomerization catalyst (III) according to claim 1, wherein the component (C) is the organoaluminum oxy-compound (c-2).

4. The olefin oligomerization catalyst (III) according to claim 1, wherein the transition metal compound (D) is a transition metal compound having a transition metal atom selected from Group III to Group VI of the periodic table.

5. A method for producing an olefin oligomer, wherein an oligomerization reaction of an olefin is performed in the presence of the olefin oligomerization catalyst (III) according to claim 1.

6. The method for producing an olefin oligomer according to claim 5, wherein the olefin is ethylene, and the olefin oligomer is 1-hexene.

* * * * *